United States Patent
Lane et al.

(10) Patent No.: US 8,900,850 B2
(45) Date of Patent: Dec. 2, 2014

(54) LATERAL FLOW BASED METHODS AND ASSAYS FOR RAPID AND INEXPENSIVE DIAGNOSTIC TESTS

(76) Inventors: Michael J. Lane, Baldwinsville, NY (US); Brian D. Faldasz, Littleton, MA (US); Jerrie Gavalchin, Groton, NY (US)

(*) Notice: Subject to any disclaimer, the term of this patent is extended or adjusted under 35 U.S.C. 154(b) by 182 days.

(21) Appl. No.: 12/807,978

(22) Filed: Sep. 17, 2010

(65) Prior Publication Data
US 2011/0165559 A1 Jul. 7, 2011

Related U.S. Application Data

(60) Provisional application No. 61/276,851, filed on Sep. 17, 2009.

(51) Int. Cl.
| | |
|---|---|
| C12M 1/00 | (2006.01) |
| C12M 1/34 | (2006.01) |
| C12Q 1/68 | (2006.01) |
| G01N 33/53 | (2006.01) |
| G01N 33/542 | (2006.01) |
| C07H 21/02 | (2006.01) |
| G01N 21/75 | (2006.01) |
| B01L 3/00 | (2006.01) |
| G01N 33/569 | (2006.01) |
| G01N 33/558 | (2006.01) |

(52) U.S. Cl.
CPC ........ *G01N 33/558* (2013.01); *G01N 33/56972* (2013.01)
USPC ........... 435/283.1; 435/6.1; 435/7.1; 435/7.9; 435/287.1; 536/23.1; 422/400; 422/420; 422/430

(58) Field of Classification Search
USPC ......... 435/6.1, 7.1, 7, 283.1, 287.1; 536/23.1; 422/400, 420, 430
See application file for complete search history.

(56) References Cited

U.S. PATENT DOCUMENTS

| | | | |
|---|---|---|---|
| 4,216,245 A | 8/1980 | Johnson | |
| 4,366,241 A | 12/1982 | Tom et al. | |
| 4,632,901 A | 12/1986 | Valkirs et al. | |
| 5,541,069 A * | 7/1996 | Mortensen et al. | 435/7.9 |
| 5,902,724 A | 5/1999 | Lane et al. | |
| 6,245,513 B1 | 6/2001 | Lane et al. | |
| 6,479,246 B1 | 11/2002 | Bessos et al. | |

(Continued)

FOREIGN PATENT DOCUMENTS

WO WO2009/005552 1/2009

OTHER PUBLICATIONS

Balakrishnan, P. et al (2005) Low-cost monitoring of HIV infected individuals on highly active antiretroviral therapy (HAART) in developing countries Indian J Med Res 121:345-355.

(Continued)

*Primary Examiner* — Narayan Bhat
(74) *Attorney, Agent, or Firm* — Klauber & Jackson LLC

(57) ABSTRACT

The invention provides reagents and methods for lateral flow assays and quantitative capture or determination of components, including cells, in a sample. In one aspect, reagents and methods for diagnostic assay are provided. In one embodiment an assay for determining T cell numbers, particularly a CD2+ CD4+ T cell assay is provided. A manufacturing method for producing rapid diagnostic assays in a decentralized manner is also described. The method generates net economic advantages over conventional diagnostic manufacturing practices.

16 Claims, 12 Drawing Sheets

(56) References Cited

U.S. PATENT DOCUMENTS

| | | | |
|---|---|---|---|
| 2003/0124739 A1* | 7/2003 | Song et al. | 436/514 |
| 2006/0240569 A1* | 10/2006 | Goldenbaum et al. | 436/514 |
| 2007/0042441 A1* | 2/2007 | Masters et al. | 435/7.5 |
| 2010/0143905 A1 | 6/2010 | Lane et al. | |

OTHER PUBLICATIONS

Baradaran, B.; Majidi, J.; Abdolalizadeh, ZM.hassan; Abdolalizadeh, J. (2005) Large Scale Production and Characterization of Anti-Human IgG. Monoclonal Antibody in Peritoneum of Balb/c MICE. Amer Journal of Biochem & Biotech 1(4):189-192.

Bendavid, E. et al (2008) Cost-effectiveness of HIV monitoring strategies in resource-limited settings: a southern African analysis Arch. Internal Med 168(17):1910-1918.

Bentwich Z (2005) CD4 measurements in patients with HIV: are they feasible for poor settings? 2(7):e214.

Branson, B.M. (2004) FDA approves OraQuick for use in saliva. Aids Clin Care 16(5):39.

Brooks, DE et al. (1999) RAMP(TM): A Rapid, Quantitative Whole Blood Immunochromatographic Platform for Point-of-Care Testing Clin Chem 45(9):1676-1678.

Cairo, CW et al (2002) Control of multivalent interactions by binding epitope density J Am Chem Soc 124(8):1615-1619.

Carriére, D et al (1999) Whole blood capcellia CD4/CD8 immunoassay for enumeration of CD4+ and CD8+ peripheral T lymphocytes Clin Chem 45(1):92-97.

Chan, CP et al. (2003) Development of a quantitative lateral-flow assay for rapid detection of fatty acid-binding protein J Immunol Methods 279(1-2):91-100.

Constantine, NT and Zink, Z (2005) HIV testing technologies after two decades of evolution Indian J Med Res 121(4):519-538.

Constantine, NT et al (2005) Update on the laboratory diagnosis and monitoring of HIV infection Cell Research 15(11-12):870-876.

Dam, TK et al (2000) Binding of multivalent carbohydrates to concanavalin A and *Dioclea grandiflora* lectin. Thermodynamic analysis of the multivalency effect J Biol Chem 275(19):14223-14230.

Daniak, MB et al (2006) Detachment of affinity-captured bioparticles by elastic deformation of a macroporous hydrogel PNAS USA 103(4):849-854.

Gestwicki, JE et al (2002) Influencing Receptor—Ligand Binding Mechanisms with Multivalent Ligand Architecture J Am Chem Soc 124(50):14922-14933.

Glencross, CF et al (2002) CD45-assisted PanLeucogating for accurate, cost-effective dual-platform CD4+ T-cell enumeration Cytometry 50(2):69-77.

Gowers, DM et al (1999) Towards mixed sequence recognition by triple helix formation Nucleic Acids Res 27(7):1569-1577.

Greenwald JL, Burstein GR, Pincus J and Branson B. A rapid review of rapid HIV antibody tests. Current Infectious Disease Reports (2006) 8, 125-131.

Griffith, BR et al (2004) A polymer scaffold for protein oligomerization J Am Chem Soc 126(6):1608-1609.

Hackbarth JS, Lee SH, Meng XW, Vroman BT, Kaufmann SH, Karnitz LM. (2004) S-peptide epitope tagging for protein purification, expression monitoring, and localization in mammalian cells Biotechniques 37(5):835-839.

Hogg, PJ et al (1985) Effects of ligand multivalency in binding studies: a general counterpart of the Scatchard analysis Biochem Biophys acta 843(3):159-163.

Hubble, J (1995) A model for the initial phase of cell/surface interactions based on ligand binding phenomena Biochem J 311 (Pt 3)::917-919.

Hubble, J (1997) Dissociation of multivalent antibody-antigen interactions Immunol Today 18(6):305-306.

Hubble, J (1999) A model of multivalent ligand:receptor equilibria which explains the effect of multivalent binding inhibitors Molecular Immunology 36(1):13-18.

Imade, G.E. et al (2005) Comparison of a new, affordable flow cytometric method and the manual magnetic bead technique for CD4 T-lymphocyte counting in a northern Nigerian setting P. Clin Diagn Lab Immunol 12(1):224-227.

Jacobs, E et al (2001) Implementation, management and continuous quality improvement of point-of-care testing in an academic health care setting Clin Chim Acta 307(1-2):49-59.

Jani, I., Janossy, G., Iqbal, A., Mhalu, F.S., Lyamuya, E.F., Biberfeld, G., Glencross D.K., Scott L.E., Reilly, J.J., Granger, V. & Barnett, D. (2001) Affordable CD4+ T cell counts on 'single-platform' flow cytometers II. The use of fixed whole blood in resource poor settings. Journal of Immunological Methods 257:145-154.

Jani, I., Janossy, G., Brown DWG and Mandy F (2002) Multiplexed Immunoassays by Flow Cytometry for Infectious Diseases in Resource Poor Settings. Lancet Infectious Diseases 2:35-43.

Kannangai et al (2001) Correlation of CD4(+) T-Cell counts estimated by an immunocapture technique (Capcellia) with viral loads in human immunodeficiency virus-seropositive individuals Clin Diagn Lab Immunol 8(6):1286-1288.

Khandjian EW, Méric C. (1986) A procedure for Northern blot analysis of native RNA. Anal.Biochem. 159: 227-232.

Kidd, P.G. et al (1993) Prediction of CD4 count from CD4 percentage: experience from three laboratories AIDS 7(7):933-940.

Kiessling, LL et al (2000) Synthetic multivalent ligands in the exploration of cell-surface interactions Curr Opin Chem Biol 4(6): 696-703.

Liang, R et al. (1997) Polyvalent binding to carbohydrates immobilized on an insoluble resin Proc Natl Acad Sci USA 94(20):10554-10559.

Ming, F et al. (2000) The kinetics of affinity-mediated cell-surface attachment Enzyme and Microbial Technology 26(2-4):216-221.

Mourez, M et al (2001) Designing a polyvalent inhibitor of anthrax toxin Nature Biotech 19(10):958-961.

Pattanapanyasat, K. et al (2005) Cytometry Part B: A multicenter evaluation of the PanLeucogating method and the use of generic monoclonal antibody reagents for CD4 enumeration in HIV-infected patients in Thailand Clinical Cytometry 65B:29-36.

Pattanapanyasat, K et al (2005) CD4+ T cell count as a tool to monitor HIV progression & anti-retroviral therapy Indian J Med Res 121(4):539-549.

Qian, S et al (2003) A mathematical model of lateral flow bioreactions applied to sandwich assays Anal Biochem 322(1):89-98.

Qian, S et al (2004) Analysis of lateral flow biodetectors:competitive format Anal Biochem 326(2):211-24.

Schweitzer, B et al (2000) Immunoassays with rolling circle DNA amplification: a versatile platform for ultrasensitive antigen detection PNAS 97(18):10113-10119.

Sulzer, Bet al (1997) Immunons revisited: binding of multivalent antigens to B cells. Mol Immunol 34(1): 63-74.

Terskikh, AV et al (1997) "Peptabody": a new type of high avidity binding protein PNAs 94(5):1663-1668.

von Lode, P (2005) Point-of-care immunotesting: approaching the analytical performance of central laboratory methods Clin Biochem 38(7):591-606.

Zeytinoglu, A et al. (2006) Comparison of *Brucella* immunoglobulin M and G flow assays with serum agglutination and 2-mercaptoethanol tests in the diagnosis of brucellosis Clin Chem Lab Med 44(2):180-184.

* cited by examiner

Figure 1. Schematic of prototype lateral flow CD4+ T cell counting assay.

Figure 2. Schematic depiction of testing Streptavidin-d(T)35 conjugate.

Printed biotinylated anti-CD4

FIGURE 10
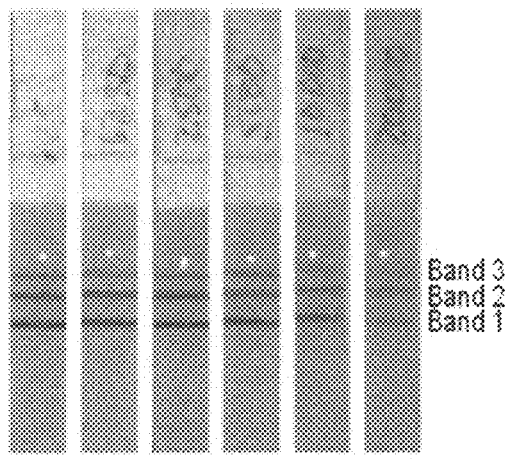
A. Polyd(A) Concentration (nanograms/100uL)
68.8  34.4  17.2  0.86  0.43  0.22
Band 3
Band 2
Band 1
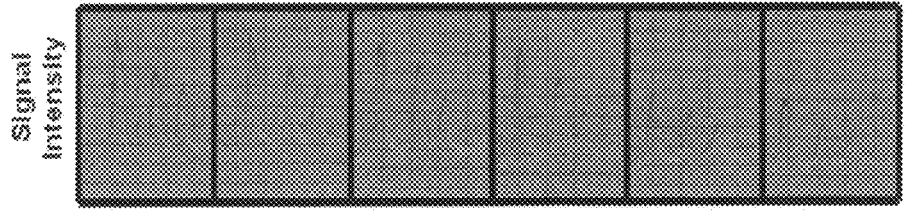
B. Polyd(A) Concentration (nanograms/100uL)
68.8  34.4  17.2  0.86  0.43  0.22
Signal Intensity
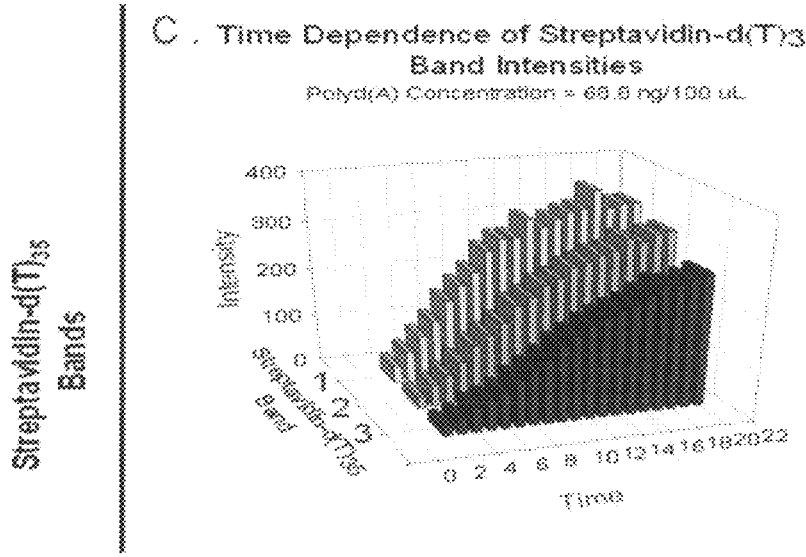
C. Time Dependence of Streptavidin-d(T)$_{35}$ Band Intensities
Polyd(A) Concentration = 68.8 ng/100 uL
Streptavidin-d(T)$_{35}$ Bands FIGURE 12
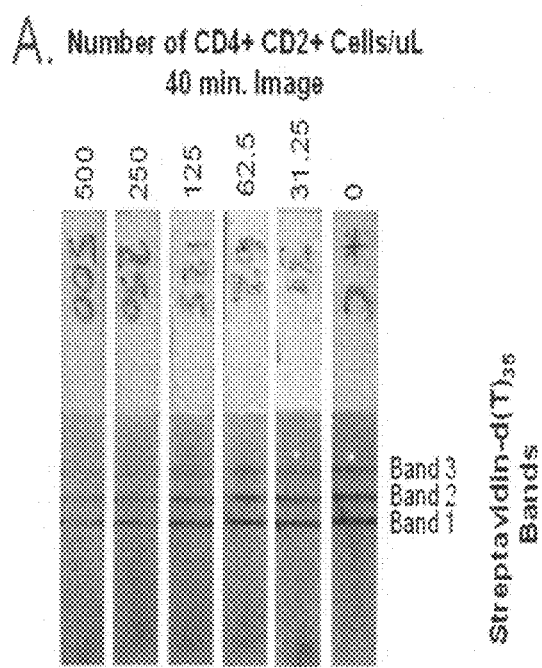
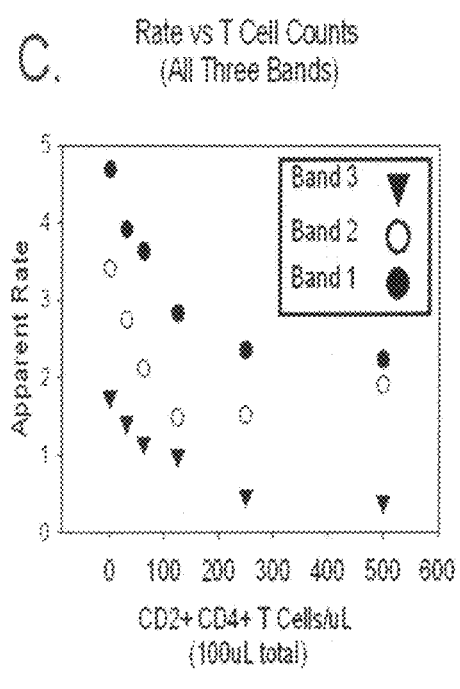
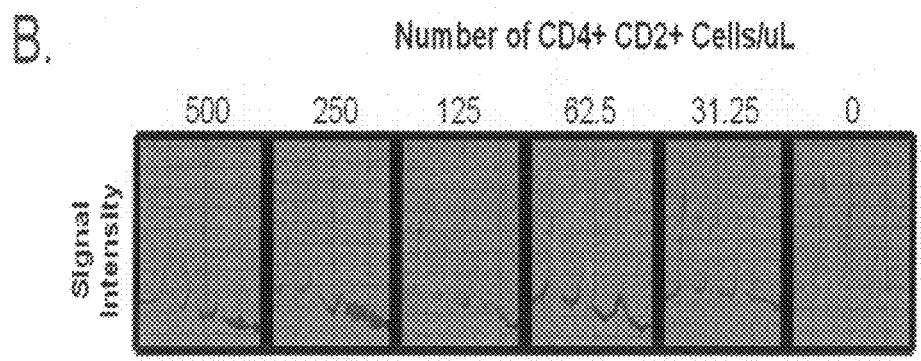

LATERAL FLOW BASED METHODS AND ASSAYS FOR RAPID AND INEXPENSIVE DIAGNOSTIC TESTS

CROSS-REFERENCE TO RELATED APPLICATIONS

The present application is a non-provisional application claiming the priority of provisional application Ser. No. 61/276,851, filed Sep. 17, 2009, the disclosure of which is incorporated by reference herein in its entirety. Applicants claim the benefits of this application under 35 U.S.C. §119 (e).

GOVERNMENT SUPPORT

The research leading to the present invention was supported, at least in part, by a grant from NIAID, Grant No. 2R42A1073220. The United States Government has certain rights in the invention.

FIELD OF THE INVENTION

The present invention relates generally to reagents and methods for lateral flow based assays which are capable of detecting specific cells or a specific cell population in a sample, including a blood sample. The method utilizes movement of cells in a sample on a surface, such as a filter, over the surface propelled by liquid flow pressure. In one aspect, reagents and methods for diagnostic assay are provided. A method for producing rapid diagnostic assays in a decentralized manner is also described. The method generates net economic advantages over conventional diagnostic assays and practices.

BACKGROUND OF THE INVENTION

The total HIV positive patient population worldwide is in excess of 40 million. The vast majority of individuals living with this disease are in resource poor environments where conventional CD4+ T cell enumeration is both too expensive to perform and technically challenging, due to a paucity of trained personnel. Treatment efforts currently underway, such as the World Health Organizations "3 by 5" Initiative, will be providing access to HAART (e.g. highly active anti-retroviral therapy) to millions of patients in these areas of the world over the next several years. It is in such resource-poor environments where CD4 counts are arguably the most important to perform. Current costs and assay complexities limit this. An accurate CD4 count can be employed: to facilitate AIDS surveillance; to monitor the rate of progression to AIDS, to define when therapy is required to prevent opportunistic infections, to place drug-naive patients into cohorts prior to therapy, and to monitor the effects of anti-retroviral therapy (c.f. Jani et al., 2001, 2002; affordCD4.com, Bendavid et al., 2008). It is currently recommended that a CD4 assay should be performed on every HIV-infected individual every 3-6 months (MMWR; 1997; 46:1) and more frequently depending on circumstance. Current available test are costly and require trained personnel to perform, generating a worldwide need for cheaper and simpler tests and assay methods.

In view of the aforementioned deficiencies and costs attendant with prior art assays and methods of manufacturing assays, it should be apparent that there exists a need in the art for simple, rapid, highly sensitive, and low cost lateral flow based assays as well a method to manufacture and analyze the results quickly and at low cost without the requirement of on site highly skilled personnel. The assay described here is intended to answer this need, both from the standpoint of addressing the technical difficulties and the requirement for low cost.

The citation of references herein shall not be construed as an admission that such is prior art to the present invention.

SUMMARY OF THE INVENTION

The invention relates generally to reagents, methods and kits for multivalent binding of components in a sample. In a particular aspect of the invention, methods and kits are provided for lateral flow assays, particularly for the detection and/or quantification of cells of interest. The invention further relates to reagents and methods for quantitative capture of components in a sample, particularly cellular components in a sample, or components which are too large or bulky to reproducibly bind or affix quantitatively to a substrate or solid support. In one aspect, reagents and methods for diagnostic assay for cells, antigen, ligand, binding agent, or antibody are provided. The reagents include polymeric scaffolds for binding of components in a sample. The scaffolds may be composed or comprised of nucleic acid and/or polypeptide. Exemplary compositions of a non-natural or deliberately constructed nucleic acid-like polymeric scaffold are provided, to which multiple antibodies, peptides or other binding agents can be affixed.

The invention provides a system for the detection and quantitation of cells of interest in a sample, said system comprising:
(A) a substrate or solid support which is a wickable medium suitable for the reception, lateral flow and transport of said sample and any cells therein;
(B) a scaffold or polymer having a repeating unit, which scaffold or polymer is bound covalently or non covalently to the substrate or support of (A) and applied in bands of varying concentrations or dilutions;
(C) a first capture reagent capable of binding directly or indirectly with the cells of interest in the sample, which first reagent is bound covalently or non covalently to the substrate or support of (A);
(D) a surrogate polymer which acts as a surrogate marker and is capable of binding directly or indirectly with the cells of interest in the sample and also with the scaffold or polymer of (B); and
(E) an indicator means which indicates the amount of scaffold or polymer of (B) which is bound in the assay;
whereby the presence and amount of cells of interest in the sample is indicated by the depletion of the surrogate marker such that less surrogate marker is available for binding with the scaffold or polymer of (B) and the intensity of the indicator is reduced.

In an aspect of the invention the system is further characterized by the following:
(A) the substrate or solid support is a wickable medium;
(B) the scaffold or polymer is selected from nucleic acid, peptide, carbohydrate, and protein; and
(C) the first capture reagent is selected from antibody, antigen, peptide, nucleic acid, protein, ligand, carbohydrate, metal, fat, oil, and organic compound.

In a further aspect, a system is provided wherein the indicator means is selected from a label, radioactive element, enzyme, and dye. In a still further aspect, a system is provided wherein one or more antibody serves as a first capture reagent.

In an additional aspect of the system the antibody is attached to the scaffold or polymer by means selected from noncovalent hybridization via sugar phosphodiester backbone hairpin structures and covalent attachment via chemical means.

A system is further contemplated wherein the scaffold or polymer is nucleic acid. In a further such aspect, the nucleic acid polymer or scaffold is a defined or repeating nucleic acid sequence.

In an additional embodiment of the system, the scaffold or polymer is streptavidin poly d(T), the first capture reagent is an antibody capable of binding to an antigen expressed by the cells of interest, the surrogate polymer is poly d(A), and the indicator means is non-radioactive and non-enzymatic.

The invention provides a system for the detection and quantitation of cells of interest in a sample, in any aspect as above described for detection of CD4+ T cells in an HIV-infected individual wherein the sample is whole blood. In one aspect, the system or method of the present invention is capable of detecting and quantifying 250 CD4+ cells/ml or less in a whole blood sample.

In one such aspect, the first capture reagent of the system is an anti-CD marker antibody.

The invention provides a test kit for quantitation of one or more cell or cell-type of interest in a sample comprising:
(A) a substrate or solid support which is a wickable medium suitable for the reception, lateral flow and transport of said sample and any cells therein;
(B) a scaffold or polymer having a repeating unit, which scaffold or polymer is bound covalently or non covalently to the substrate or support of (A) and applied in bands of varying concentrations or dilutions;
(C) a first capture reagent capable of binding directly or indirectly with the cells of interest in the sample, which first reagent is bound covalently or non covalently to the substrate or support of (A);
(D) a surrogate polymer which acts as a surrogate marker and is capable of binding directly or indirectly with the cells of interest in the sample and also with the scaffold or polymer of (B); and
(E) an indicator means which indicates the amount of scaffold or polymer of (B) which is bound in the assay;
whereby the presence and amount of cells of interest in the sample is indicated by the depletion of the surrogate marker such that less surrogate marker is available for binding with the scaffold or polymer of (B) and the intensity of the indicator is reduced.

In one embodiment of the test kit provided, the scaffold or polymer is nucleic acid and the first capture reagent comprises an antibody.

In a further embodiment, the test kit is suitable for detection of CD4+ T cells in an HIV-infected individual wherein the sample is whole blood.

The invention provides a method for the manufacture of a detection and quantification strip to be used for detection and quantification of cells of interest in a sample, which strip comprises
(A) a substrate or solid support which is a wickable medium suitable for the reception, lateral flow and transport of said sample and any cells therein;
(B) a scaffold or polymer having a repeating unit, which scaffold or polymer is bound covalently or non covalently to the substrate or support of (A) and applied in bands of varying concentrations or dilutions;
(C) a first capture reagent capable of binding directly or indirectly with the cells of interest in the sample, which first reagent is bound covalently or non covalently to the substrate or support of (A);

(D) a surrogate polymer which acts as a surrogate marker and is capable of binding directly or indirectly with the cells of interest in the sample and also with the scaffold or polymer of (B); and
(E) an indicator means which indicates the amount of scaffold or polymer of (B) which is bound or unbound in the assay; comprising selecting a liquid deposition device and depositing each or any of the scaffold, first capture reagent, and indicator with said liquid deposition device in a regular and predetermined pattern.

In an aspect of the method, the liquid deposition device is an inkjet printer.

In an embodiment of the method, a method is provided wherein
(A) the substrate or solid support is a wickable medium;
(B) the scaffold or polymer is selected from nucleic acid, peptide, carbohydrate, and protein; and
(C) the first capture reagent is selected from antibody, antigen, peptide, nucleic acid, protein, ligand, carbohydrate, metal, fat, oil, and organic compound.

In an embodiment of the method, a method is provided wherein the scaffold or polymer is streptavidin poly d(T), the first capture reagent is an antibody capable of binding to an antigen expressed by the cells of interest, the surrogate polymer is poly d(A), and the indicator means is non-radioactive and non-enzymatic.

BRIEF DESCRIPTION OF THE DRAWINGS

FIG. 10. Polyd(A) dependence of printed streptavidin-d(T)$_{35}$ bands. (A) Pictures were taken with a digital camera at one-minute intervals over a period of 20 min. (t=7 min. is shown for all polyd(A) concentrations). Because the camera images were acquired through the BCIP/NBT "bead" on the strip glare (light spot) is visible on all strips. (B) Using ImageJ software, 3D surface plots were then created for every minute of each Polyd(A) concentration so signal intensity could be measured. A baseline was drawn from wing to wing under the peaks and the distance from peak to baseline was measured for each band at each time point. (C) The band intensities were plotted in a 3D bar chart versus time for each concentration of Streptavidin-d(T)$_{35}$ to show time dependence of signal increase.

FIG. 12. CD4+ CD2+ cell titration experiment at fixed polyd(A) concentration. Streptavidin-d(T)$_{35}$ bands printed at streptavidin-d(T)$_{35}$ input concentrations of 57, 28.5 and 14.25 pMoles/uL (Band 1, Band 2, and Band 3 respectively). 100 uL of pre-diluted T cells (CD2+, CD4+) in media (+10 uL of 0.5M EDTA, pH 8.0, containing 0.25 ug biotinylated anti-CD4, 57 pmoles streptavidin-d(T)$_{35}$; incubation time=15 min. RT) was carefully pipetted in ~15 uL aliquots such that the nitrocellulose remained wet throughout the process. 100 uL PBS wash solution was then flowed over the strips as a wash. Then 100 uL PBS containing 0.43 nanograms polyd (A). Next, 100 uL of d(T)20-FITC conjugate at 0.03 pMol/uL was flowed up the membrane followed by a 100 uL PBS rinse step. To detect bound d(T)20-FITC 100 uL anti-FITC:alkaline phosphatase conjugate at 0.0023 pMol/uL was flowed up the strip followed by removal of the wick placing the strip horizontal and BCIP/NBT (~150 uL was added to all strips. (A) Pictures were taken with a digital camera at one minute intervals over a period of 40 min. (B) Using ImageJ, 3D surface plots were then created for every minute of each cell concentration to allow signal intensity to be measured. A baseline was drawn from trough to trough and the distance from peak to baseline was measured for each band at every time. Signal intensities were stored in a spreadsheet and plotted over time so apparent rates could be measured. (C) Rates for each band were then plotted as a function of cell concentration.

DETAILED DESCRIPTION

Figure 1:
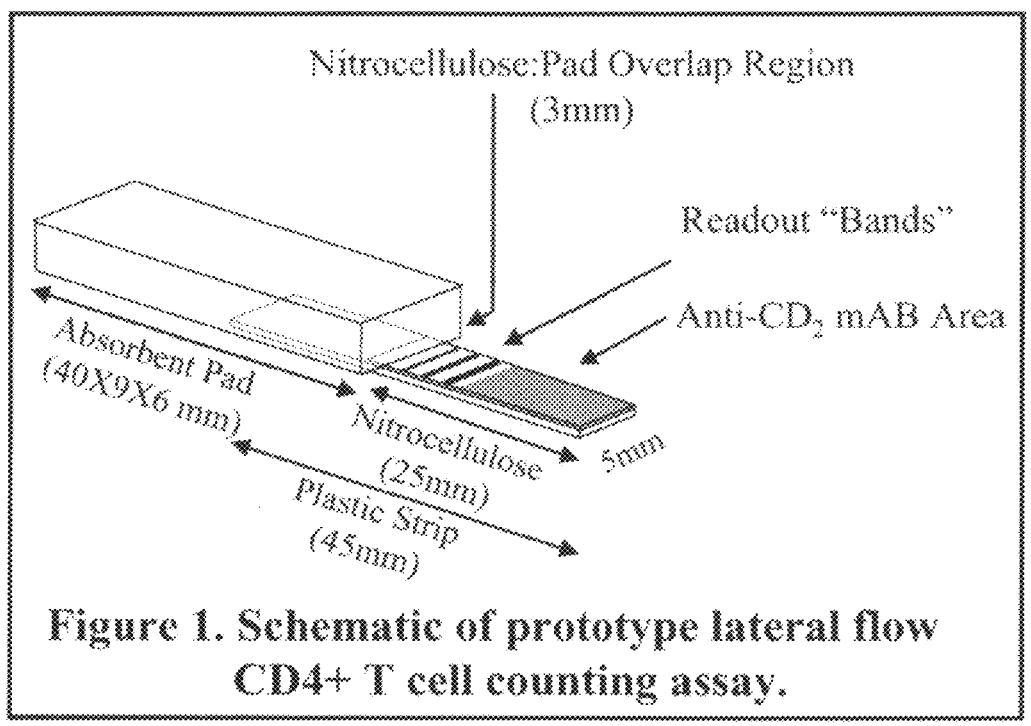
FIG. 1. Schematic of prototype lateral flow CD4+ T cell counting assay. The design incorporates anti-CD2 antibody printed on the lower half of the strip followed by three Streptavidin-$dT_{35}$ conjugate lines printed at 1.0×, 0.5× and 0.25×. (See text for detailed discussion).

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins. (1985)]; "Transcription And Translation" [B. D. Hames & S. J. Higgins, eds. (1984)]; "Animal Cell Culture"

[R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are utilizing standard protocols and terms.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The term "oligonucleotide," as used herein in referring to the probe of the invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular hybridization reaction. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA which are degenerate to those set out herein. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |

| | |
|---|---|
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in nucleic acid sequences such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein.

The following is one example of various groupings of amino acids:
Amino acids with nonpolar R groups—Alanine, Valine, Leucine, Isoleucine, Proline, Phenylalanine, Tryptophan, Methionine
Amino acids with uncharged polar R groups—Glycine, Serine, Threonine, Cysteine, Tyrosine, Asparagine, Glutamine
Amino acids with charged polar R groups (negatively charged at Ph 6.0)—Aspartic acid, Glutamic acid
Basic amino acids (positively charged at pH 6.0)—Lysine, Arginine, Histidine (at pH 6.0)
Another grouping may be those amino acids with phenyl groups: Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces-turns in the protein's structure.

Two amino acid sequences are "substantially homologous" when at least about 70% of the amino acid residues (preferably at least about 80%, and most preferably at least about 90 or 95%) are identical, or represent conservative substitutions.

The present invention should be considered to include amino acid sequences containing conservative changes which do not significantly alter the activity or binding characteristics of the resulting polypeptide, antigen or antibody. Similarly the nucleic acid sequences set out herein are exemplary and should not be interpreted as limiting. Therefore, changes, alterations, additions and deletions can be made in the sequences to alter length, G-C content, extent of hybridization, length of homologous or hybridizing nucleic acid, percent identity, degree of homology, etc.

A "heterologous" region of the nucleic acid construct is an identifiable segment of nucleic acid within a larger nucleic acid molecule that is not found in association with the larger molecule in nature. Thus, when the heterologous region encodes a mammalian gene or portion thereof, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" can include an immunoglobulin, including antibodies and fragments thereof, that binds a specific epitope. The term encompasses polyclonal, monoclonal, single chain, Fv, fragments, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules, or containing the combining site, is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. An antibody may be constructed of a plurality of antibody combining sites, each immunospecific for a different antigen; e.g., a bispecific (chimeric) monoclonal antibody.

The general methodology for making monoclonal antibodies by hybridoma technology is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399, 121; 4,427,783; 4,444,887; 4,451,570; 4,466,917; 4,472,500; 4,491,632; 4,493,890.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

The phrase "pharmaceutically acceptable" refers to molecular entities and compositions that are physiologically tolerable and do not typically produce an allergic or similar untoward reaction, such as gastric upset, dizziness and the like, when administered to a human.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$ C below the predicted or determined $T_m$ with washes of higher stringency, if desired.

The present invention relates generally to reagents and methods for lateral flow assays for determining components in a sample. The invention further relates to reagents and methods for quantitative assay of components in a sample. In one aspect, reagents and methods for diagnostic assay for quantitating cells in a sample, including blood are provided.

The current assay design was dictated by the need to move whole T cells by flow pressure over a membrane which, while allowing capture, leaves the cells spread over a 500 mm$^2$ area. Our first assay design implemented a "direct detection" strategy which used anti-CD2 antibody to capture the T cells followed by anti-CD4 as a detector. However, with the cells spread over such an area, direct detection proved to be unfeasible. The current design uses a surrogate polymer (polydeoxyadenosine) which binds both the Streptavidin-d (T)$_{35}$ labeled CD2+ CD4+ T cells and three streptavidin-d(T) $_{35}$ "bands". The amount of bound polyd(A) is then assessed. Thus, if there are many CD4+ cells bound to the anti-CD2 portion of the strip the three streptavidin-d(T)$_{35}$ bands develop more slowly. Two other groups have reported to us that they were unable to achieve cell movement using nitrocellulose membranes and, consequently abandoned this approach (PATH and Gates Foundation Imperial College CD4 group, personal communications).

The method provided uses an unconventional approach to moving cells/blood on nitrocellulose as the cells do not move through the membrane, but rather over the membrane surface, propelled by liquid flow pressure. The assay incorporates several other unique features that we believe are not found in any other lateral flow assay: 1) The current assay is manufactured using an inexpensive inkjet printer (HP DeskJet Model 3945) with standard print cartridges to print all reagents, allowing for local assay manufacture; 2) the assay employs an "indirect readout" which also provides enzyme-free signal amplification, facilitating the use of small blood samples as input (<30 uL): 3) the assay can be performed in the field and then, if desired, can be remotely analyzed by experts using a series of standard cell phone photographs taken over time and uploaded to the Internet via email.

The prototype assay design is shown in schematic form in FIG. 1. T cells are too large to enter the nitrocellulose membrane, so to move the cells across the nitrocellulose we developed a technique which allows surface movement of fluid toward the absorbent pad to move the cells along the surface of the printed anti-CD2 reagent. This appears to capture T cells quantitatively. Successive reagents are then introduced, by standard lateral flow, which lead to the indirect readout results at the streptavidin-d(T)$_{35}$ printed "bands".

This invention also provides a manufacturing method for producing rapid diagnostic assays in a decentralized manner and at low cost. The method generates net economic advantages over conventional diagnostic manufacturing practices. The methods and compositions of this invention provide a means for producing and conducting rapid and sensitive assays on site in poor, remote, low technology, or high throughput locations or situations.

Assays for multivalent binding and quantitative capture of reagents, including multivalent and scaffold components and manufacturing methods, are described in PCT/US2008/004100, published as WO 2009/005552, which is incorporated by references herein in its entirety.

Specific binding of target molecules with high avidity is of tremendous importance for effective molecular diagnostics. The ability to bind and hold targets from a relatively dilute sample (e.g., blood sample), permits concentration of these dilute targets which enables the use of detection methods that have previously only been useful for targets present in high concentrations in the sample (e.g., alkaline phosphatase and other color-generating chemistries). The cost advantages of such approaches enables high volume applications (e.g., point-of-care assays) that would otherwise be prohibitively expensive in both specialized equipment and highly-trained personnel for operation and correct interpretation of results of same. Examples include both detection and quantification of specific cell types, cancer cells, viral load, bacterial infection, biotoxins and other foreign protein targets, and inherent markers of host disease conditions (e.g., diabetes, genetic markers, various cancers, adverse cardiovascular conditions).

Purification and/or identification of specific cell populations such as in diagnostics, monitoring, for transplantation or other therapeutic applications offers yet another application for the present invention. High avidity binding agents, e.g., constructs of the present invention bound to a filter membrane, can allow for the extraction of desired cell populations, from blood, bone marrow or spinal fluid, for example. In a similar application, undesirable cells or proteins could be removed from the blood; for example, leukemic cells, could be removed prior to autologous bone marrow transplantation of a leukemia patient.

Requirements for detection and identification of bioterrorism, chemical warfare and explosive agents are similar to those of the most sensitive diagnostic applications. Target molecules can be expected to be highly dilute in the sample (water, air). In this application, the need for field-testing is even greater than for point-of-care diagnostics. The characteristics of the present invention enable trapping of extremely dilute target molecules for further detection or analysis.

In bioremediation, extraction of some undesirable or environmentally damaging or toxic molecules from groundwater and/or wastewater is currently both expensive and time consuming. The present invention enables more efficient and higher throughput removal of contaminants than conventional approaches by, e.g., using membranes, surfaces or filters that have been coated with the polyvalent binding constructs of the present invention and thereby obtaining a higher capture/filter efficiency at potentially higher flow volumes.

Purification of drinking water offers yet another application for the present invention. High avidity binding agents, e.g., constructs of the present invention bound to a filter membrane, can allow for the extraction of various biological and chemical molecules from the water.

The chemical and biotechnology industries routinely require extraction and concentration of molecular species to obtain pure reagents. This application of the present invention is, in effect, the reverse of the water purification application, where the molecules captured from the solution can then be further concentrated and purified.

Testing for or purification/extraction of chemical contaminants at low levels, for example the detection of antibiotics in milk and soil, pesticides and industrial pollutants in water and soil, could also be accomplished with the present invention.

Veterinary applications, including but not limited to diagnostics, pharmaceuticals and vaccines, are similar to those already described for human medical applications.

Testing for contaminants and infectious agents in meat and produce can be accomplished with the present invention, offering higher sensitivity to targets than presently available rapid tests due to the high avidity characteristics of the present invention. Targets captured for these purposes can then be further processed, e.g., as for diagnostic applications.

The present invention is particularly applicable in remote locations and in epidemic or chronic disease situations. For instance, it would be useful in HIV-prevalent or malaria-infected parts of the world for rapid, cost-effective diagnosis and assessment. In situations where there is potentially epidemic or disease, the assay and methods provide rapid, accurate and cost-effective assessment and monitoring, enabling critical treatment to those in need.

In an embodiment, the present assay or method is comprised of: 1) a monovalent antibody constructed as described here and employed as a capture antibody construct; 2) an antigen, that is, a target molecule or cell of interest; and 3) a multivalent or polyvalent antibody constructed as described here and employed as a detection antibody construct.

In this embodiment, the detection antibody construct has been further modified so as to provide a means for signaling its presence, e.g., by means of direct attachment of dye (visible, fluorescent, phosphorescent, etc.) molecules.

In the descriptions that follow, the term "antibody" refers generally to any of a variety of molecules that specifically recognize and bind preferentially to one chemical or molecular species. It is clear to one skilled in the art that, in addition to biological antibodies or immunoglobulins as noted above, also included in the term "antibody" as used herein are peptides, polypeptides, proteins, and other molecular moieties having the capability of preferential recognition and binding to particular molecular species. Further and similarly, the term "antigen" refers generally to any of a variety of binders or molecules that are recognizable as distinct entities or families of entities by an antibody (as defined above), and can include peptides, nucleic acids, metals, carbohydrates, fats, oils, etc.

In another embodiment, the signaling means employs any of a variety of signal amplification methods and/or compositions, numerous examples of which are well known to those skilled in the art.

In any of the above in vivo aspects, addition or incorporation of a label, radioactive element, enzyme or dye provides for imaging or detecting binding in vivo. The label may be selected from enzymes, ligands, chemicals which fluoresce, radioactive elements etc. In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The invention provides a method and means for the manufacture of diagnostic test or ligand capture strips, sheets or surfaces. The method or means includes a medium for deposition, a liquid deposition device for depositing, and a reagent to be deposited. The liquid deposition device includes any device capable of depositing small quantities of liquid, which can be directed to deposit the liquid in a regular or programmable pattern. In order for the test strips to be affordable (i.e. relatively low cost) and manufacturable at most locations, including remote and less civilized locations, quickly and without much operator intervention, the device should be inexpensive, relatively small in size, portable, programmable, and simple to operate. Exemplary preferred devices include printers, particularly inkjet printers, and particularly wherein the printer can be used with replaceable cartridges. A particularly preferred inkjet printer is the Hewlett-Packard deskjet printer. An additional preferred inkjet printer is a Lexmark printer.

A diagnostic test strip includes any regular or predetermined pattern of reagent(s) applied to a medium, including paper, nylon, plastic, filter or other surface. The regular or predetermined pattern may be lines, dots, bars, boxes, letters, symbols or images and can be placed in a linear, vertical, horizontal, circular or angled pattern.

Reagent(s) include a ligand, antigen, receptor, antibody, peptide, target sequence, active site, lectin, a component in a multicomponent complex, etc., in other words any component which can be bound to or by or otherwise stably interact with another component in a sample, solution or mixture.

The pattern may incorporate one or more than one reagent(s). Thus one reagent may be printed in a particular pattern or location and a second, third, etc. reagent may be printed in a different location or pattern. Instead of printing individual strips for each diagnostic or assay, for example, one strip can be printed in a series of lines running horizontally (e.g., bottom to top) or as vertical lines or locations next to one another (e.g. left to right). In this manner a test strip can assay for multiple components or diagnose for multiple diseases simultaneously. Each location or line indicates the presence or amount of a different component. Thus, a single test strip can cost-effectively and simultaneously assay, for example, for HIV, hepatitis B, hepatitis C, influenza, etc., as in a blood testing situation. One approach to such a multi-reagent printing is to utilize the different color vials (e.g. cyan, magenta, yellow) in a color inkjet printer. Each color vial can print a different reagent or can be used to print different combinations of reagents. Alternatively, the strip may be consecutively printed by reloading the print medium or paper and printing a different reagent on the strip as in overprinting. The inventors have successfully overprinted over a dozen times without problems.

Also, the printer may use a multi-component reagent, as in for instance a library of antigens, peptides, compounds or phage to print on a strip. The antibody or binder will bind to its target from the multi-component mix on the strip. The antibody or binder can then be released physically or chemically.

The medium includes paper, particularly paper which has a nylon, acrylic, plastic or other water-resistant or protective surface or coating. The paper includes inkjet paper, glossy paper, Whatman paper. Track etched membranes may also be used.

A conventional (e.g. first world) manufacturing and distribution model for rapid diagnostic test manufacture and development involves a centralized manufacturing facility where components are assembled. Assembled components are then distributed from the central location. The need for up-front acquisition of expensive manufacturing equipment to manufacture such assays can create a formidable barrier to assay deployment. To address this issue, we propose a rapid diagnostic assay-manufacturing model in which a liquid deposition device, an inkjet printer for example, is employed to "print" such assays with components either obtained from a quality controlled central source or locally manufactured. To address the issue of manufacturing equipment expense, we employed (as an example, although not limiting in the current invention) a low-end HP deskjet printer for deposition of the capture reagent on such assays. Advantages of the method include that no modifications to the printer are required and antibody printing involves simply replacing the ink in an HP27 (black ink cartridge) with the capture antibody solution.

This invention provides for the use or modification of an existent printer, particularly an inkjet printer, and/or construction of a new printer which provides the user with a relatively simple and portable manufacturing approach to immunochromatographic diagnostic assay manufacture.

The various aspects of the present invention allow for a method for distributed manufacture of diagnostic tests comprised of a test format amenable to local manufacture and execution, e.g., the methods of the present invention; an inkjet printer; printable test media; a mixture containing antibodies and/or antibody constructs amenable to inkjet printing, said mixture being in any of a variety of forms include frozen, liquid, or dried which would require rehydration prior to use; various other test components as anticipated by the methods of the present invention; and a pattern or program for printing, which may be encoded in a computer system attached to the printer (e.g., a figure in a drawing program) or may be encoded on a memory card for which an interface slot is provided on the printer, or by other encoding means known in the art. This method offers economic benefits by permitting distribution of the various components to the test manufacture site, even permitting such distribution from multiple, disparate sources. Further benefits accrue from the use of local (to the point of manufacture or point of use) personnel at prevailing, local wage factors, thereby offering significant cost reduction over a single point of manufacture.

The methods for distributed manufacture of diagnostic tests may include use of software that permits or requires license enforcement for licenses regarding the manufacture and use of a diagnostic test that includes license terms, which software may use communications facilities, e.g., the Internet, to communicate with a licensing authority to permit manufacture of the test or to control aspects of the test manufacture, e.g., the number of tests that may be printed.

Local manufacture can include, for example, manufacture of the assembly in proximity to the location at which the diagnostic test will be executed, e.g., at a doctor's office, at a clinic, at a local warehouse, etc. The more remote the location, the greater the advantage conferred by the present invention.

Advantages conferred by the present invention include, but are not limited to, economic advantages, e.g., local manufacture is often less expensive than centralized manufacture and distribution; shipping of components instead of completed assemblies permits choice of shipping method for each type of component, thereby further increasing the economic advantage; and, local assembly permits shipping of components in their most stable forms.

In one embodiment, the present invention is comprised of a system of aspects working cooperatively to effect the local manufacture and assembly of the diagnostic assay. The aspects are delineated below, and it is obvious to one skilled in the art that the order of presentation does not imply or suggest priority or prerequisite of one aspect over another unless explicitly indicated.

One aspect of the present invention employs a device for liquid deposition onto a medium, for instance but not limited to, an inkjet printer, which is used to apply capture reagents onto the medium in repeatable volumes over repeatable patterns, e.g., bands, spots, lines, or other such shapes and/or layouts as are required by the diagnostic assay. The deposition device may include a computer system to provide control over the deposition process, or the pattern or patterns may be defined on a memory device which is plugged into or is otherwise read by a printer or other deposition device, or, the printer or deposition device itself may have, internally defined, controlling patterns for deposition.

Another aspect of the present invention employs a medium which is useful for creating lateral flow diagnostic tests, for instance but not limited to nitrocellulose-coated acrylic, upon which the aforementioned liquid deposition device may deposit diagnostic reagents in patterns, e.g., bands, spots, lines, or other such shapes and layouts as are required by the diagnostic assay. For purposes of the present discussion, medium upon which has been deposited diagnostic reagents is called "printed medium".

Another aspect of the present invention includes a reagent or reagents that will be deposited upon the aforementioned medium to effect a critical component of the diagnostic assay, e.g., the target capture reagent. These reagents may be liquid or solid, and may be packaged in a form, e.g., solid, which is particularly resilient in shipping, and which is then resuspended in liquid form prior to introduction into the aforementioned liquid deposition device. Alternatively, these reagents may be shipped at a higher concentration of active ingredient(s) than will be used in the actual assay, thereby reducing the volume and/or weight of material to be shipped.

Yet another aspect of the present invention is comprised of any of a number of different methods for shipping materials, reagents and/or equipment ("material"), including, but not limited to, trucking or automotive, train, and aircraft, including both private and commercial providers of such shipping methods, or combinations thereof.

In a preferred embodiment of the present invention, the various matter comprising the diagnostic test components are shipped to a local manufacture site, at which the components are assembled, e.g., resuspension of capture reagents; the component(s) to be deposited onto the printed medium is/are placed into the liquid deposition device; the liquid deposition device is employed to deposit the components onto the medium, thereby resulting in printed medium; the printed medium is assembled with other required components thereby resulting in a complete diagnostic assay.

In a preferred embodiment, the liquid deposition device is an inkjet printer.

In another embodiment, the liquid deposition device is a device specifically designed to perform the manufacturing task of the present invention.

In another embodiment, liquid deposition device is programmed to require an operator validation step, part of which may optionally include requiring communication with an intellectual property holder to enable licensed printing of one or more printed medium.

In another embodiment of the present invention, the liquid deposition device obtains, either with or without operator intervention, patterns for deposition and/or license information for validation and enforcement by means of any of a variety of communications devices known in the art; for example, the device may require entry of a validation code that has been obtained by any communication means, so that the device is enabled to perform the liquid deposition. Further, the device may obtain, by any communication means, patterns for deposition of the materials specific to the particular assay under manufacture.

In another embodiment, the communication means includes any of telephone, satellite phone, Internet, cellular phone, wireless network, wireless device, Bluetooth, or network.

As suggested earlier, the diagnostic method of the present invention comprises examining a cellular sample or medium by means of an assay including a means for lateral flow. Patients or individuals capable of benefiting from this method include those suffering from cancer, a pre-cancerous lesion, a viral infection, a bacterial infection or other like pathological derangement.

As used herein, "pg" means picogram, "ng" means nanogram, "ug" or "µg" mean microgram, "mg" means milligram, "ul" or "µl" mean microliter, "ml" means milliliter, "l" means liter.

The labels most commonly employed for in the assays and methods of the invention are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit or anti-mouse antibody prepared in goats or other animals and conjugated with fluorescein through an isothiocyanate. The scaffold or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared. In accordance with the testing techniques discussed above, one class of such kits will contain at least a labeled antibody or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined binding activity, comprising:
(a) a test strip manufactured or formatted as described herein;
(b) a predetermined amount of at least one labeled immunochemically reactive component obtained by the direct or indirect attachment of the antibody or a specific binding partner thereto, to a detectable label;
(c) other reagents; and
(d) directions for use of said kit.

More specifically, the diagnostic test kit may comprise:
(a) a test strip manufactured or formatted as described herein;
(b) a known amount of the antibody as described above (or a binding partner) generally bound to a solid phase to form an immunosorbent, or in the alternative, bound to a suitable tag, or plural such end products, etc. (or their binding partners) one of each;
(c) if necessary, other reagents; and
(d) directions for use of said test kit.

In accordance with the above, an assay system for screening potential drugs effective to modulate the activity of the antibody or target may be prepared.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE

Currently, the cost of CD4+ T cell counting, for monitoring of AIDS patients, is a major issue (especially) in resource-poor environments, where HIV infection rates are highest. Additionally, for assays developed to date, personnel need to be trained to use relatively complex equipment (cytometers, cell sorters, plate readers, etc.) and most such equipment demands a controlled environment for proper functioning. The present invention is aimed at development of a rapid CD4+ T cell counting assay that addresses these concerns, and is based on the lateral flow approach. The critical features of the assay are 1) the assay can be manufactured locally (if desired), 2) the assay can be run on "finger stick" sized blood samples (i.e. 30 uL or less) and 3) the test results can be interpreted by trained personnel by transmission of a series of cell phone images to a remote server for an expert to analyze. We suggest that an accurate CD4 counting assay with these attributes might be manufactured that would cost the end-user less than US $1.00 per test.

We have developed a prototype lateral flow CD4+ T cell assay that is capable of enumerating human Jurkat cells (CD2+, CD4+) spiked into whole chicken blood with a 30 minute readout. The assay incorporates several unique features that we believe are not found in any other lateral flow assay. These are:

1) The reagents in the rapid assay can be printed using an inexpensive inkjet printer with standard print cartridges, allowing for local assembly of the assay, if desired,
2) The assay employs an "indirect readout" which provides enzyme-free signal amplification, facilitating the use of small blood samples as input (10-20 uL),
3) The assay can be performed in the field and then can be remotely analyzed by experts using a series of standard cell phone photographs taken over time and uploaded to the Internet via email. CD4+ T cells/uL are determined in a standardized fashion by analyzing signal increase over time (i.e. rates of color development from three indirect readout "bands" on the nitrocellulose strips).

The prototype assay design is shown in schematic form in FIG. 1.

T cells are too large to enter the nitrocellulose membrane. To move the cells across the nitrocellulose we add the cells to the pre-saturated membrane (in the anti-CD2+ region), which allows surface movement of fluid toward the absorbent pad to move the cells along the surface of the printed anti-CD2 reagent, which appears to successfully capture T cells quantitatively. Successive reagents are introduced, by standard lateral flow which lead to the indirect readout results by the streptavidin-d(T)35 lines.

Background and Significance

The total HIV positive patient population worldwide is in excess of 40 million. The vast majority of individuals living with this disease are in resource poor environments where conventional CD4+ T cell enumeration is both too expensive to perform and technically challenging, due to a paucity of trained personnel. Treatment efforts currently underway, such as the World Health Organizations "3 by 5" Initiative, will be providing access to HAART (e.g. highly active anti-retroviral therapy) to millions of patients in these areas of the world over the next several years. It is in such resource-poor environments where CD4 counts are arguably the most important to perform. Current costs and assay complexities limit this. An accurate CD4 count can be employed: to facilitate AIDS surveillance; to monitor the rate of progression to AIDS, to define when therapy is required to prevent opportunistic infections, to place drug-naive patients into cohorts prior to therapy, and to monitor the effects of anti-retroviral therapy (c.f. Jani et al., 2001, 2002; affordCD4.com, Ben-david et al., 2008). It is currently recommended that a CD4 assay should be performed on every HIV-infected individual every 3-6 months (MMWR; 1997; 46:1) and more frequently depending on circumstance. The assay described here is intended to answer this need, both from the standpoint of addressing the technical difficulties and the requirement for low cost.

Currently Available CD4 Tests

Current CD4 counting assays are expensive, especially in resource poor settings and generally require some technological sophistication for assay execution. The gold standard for such testing is cell sorting. Currently available assays and their estimated costs are summarized in Table 1.

TABLE 1

CD4 Tests and Their Cost[1]

| Test | Manufacturer | Equipment Required | Cost* |
| --- | --- | --- | --- |
| FACS Count | Becton Dickinson | Flow cytometry instrument, automated | US $40.00 |
| Cytosphere | Beckman Coulter | Microscope, haemocytometer, manual | US $15.00 |
| Dynabeads CDF/CD8 | Dynal | Mixer, magnet, microscope, manual | US $16.00 |
| Capcellia | BioRad | Plate reader, magnet, multichannel pipette; manual | US $40.00 |
| Easy CD4/CD8 | Guava Technologies | Micro cytometry instrument, computer, semi-automated | US $40.00 |
| Partec CyFlow | Partec | Dedicated cytometer, computer, semi-automated | US $40.00 |

*Approximate costs adapted from Balikrishnan et al, 2005
[1]Note: Constantine et al, 2005 also list the following tests as available: Opti-CIM (CIMA, light microscopy, price not available), Zymmune (Zynaxis Corp, withdrawn from market), TRAxCD4 (T Cell DXs and Immunogenetics; withdrawn from market), CD4 Count Chip (SemiBio, no pricing available) and CD4 Biochip (Labnow, launch this year, pricing unavailable). Also, cited pricing varies from source to source although the $3-10 range is agreed upon for most manual tests.

Table 1 illustrates that even the "lower cost" tests represent a significant cost burden in resource poor environments. Even the lowest cost test (not accounting for labor) is of significant cost with respect to the estimated $181.00 per patient year expected expense for ART therapy once local drug manufacturing is available (Badri et al., 2006) if CD4 counts are to be useful for monitoring infected individuals. It is also significant that all of the tests described above require some type of instrumentation with attendant training and specialized environment associated with its use (for review see Balkrishnan et al., 2005; Constantine and Zink, 2005).

A variety of approaches to reduce costs in existing assays have been reported (reviewed in Rodriguez et al., 2005). "PanLeucogating" (c.f. Glencross et. al., 2002) and use of "generic", i.e. not proprietary, antibodies (c.f. Pattanapanyasat et al. 2005) have both been evaluated; however, the need for additional commercial reagents and the "center-based"

deployment of cytometric devices is a difficult burden to overcome. A prototype microchip based methodology for CD4 counting in resource-limited environments has recently been described (Rodriguez et al., 2005), however, as has been pointed out by others (Bentwich, 2005), the final cost of the device and associated reagents is unknown at this time.

We provide a simple lateral flow test for CD4 enumeration. Lateral flow point of care assays have become commonplace in drug testing, pregnancy testing, etc. and have been shown to be remarkably robust to the variation they are exposed to as home test solutions (c.f. Zeytinoglu et al., 2006) if care is taken in assay design (Jacobs et al., 2001). Such assays, when sold in the first world, are generally one-step sample application (blood, urine, saliva, etc.) tests with the assay encased in plastic (reviewed in von Lode, 2005).

In the ideal case, a CD4 assay suitable for resource poor environments would have several critical attributes. In this section, these attributes are described and an approach to fulfilling them is delineated. Our overall design is based on the "Capcellia" strategy which employed an anti-CD2 monoclonal antibody to capture all T-cells and a secondary (anti-CD4/CD8) "staining" antibody (Carrière et al., 1999; Kannangai, 2001).

Attribute 1.

The assay must be easy to manufacture; the sheer volume of required tests is daunting. Approach: A conventional (e.g. first world) manufacturing and distribution model is not appropriate for this volume of tests, if they are to be made available in a timely fashion. Therefore, one parameter that must be considered is that the test must be capable of being manufactured locally on an "as needed" basis. An important aspect of this attribute is that the need for up-front acquisition of expensive manufacturing equipment to manufacture the assay must be minimized or eliminated. To address this, we propose a lateral flow assay (plastic-backed nitrocellulose strip) with ink-jet deposition of the CD4+ T cell capture (avidity) reagents. We have already defined the "strip" size such that a total of 50 assays can be printed per Millipore Hi-Flow "card" of 10 mil plastic backed nitrocellulose. To address the issue of equipment expense and accessibility to manufacturing of the assay, we have employed a low-end HP deskjet printer (DeskJet Model 3945; US$ 39.90; Wal-Mart) for deposition of the capture reagent. No modifications to the printer are required and antibody printing involves simply replacing the ink in an HP27 (black ink cartridge) and/or the tri-color cartridge with the capture antibody solution (at appropriate concentration). For test design and printing, we employed Microsoft Powerpoint software. Printing was monitored by inclusion of trace quantities of yellow food dye.

Attribute 2.

The assay must be capable of being used in a variety of physical environments by unskilled personnel. Approach: The attribute allowing for the performance of the test by an unskilled operator is addressed by employing a simple process. First blood is placed on the strip then a four-step procedure which requires only that the operator of the test move the test strip sequentially from vial to vial, and then interpret the results by taking four cell-phone photographs and emailing them to a web address (total time ~30-40 min.). The issue of environment control in a classically distributed rapid test would lead immediately to long term stability studies with all components, especially when reagents are stored at ambient temperatures. However, the approach provided herein allows for the critical reagents to be maintained in a controlled environment up to and including a local distribution point, from which test kits can be prepared and assembled for short-term distribution and use on an "as needed" basis.

Attribute 3.

The assay must be able to "count" CD4 cells/uL at appropriate levels using a colorimetric approach to avoid the need for machine reading of test output. Approach: The ability to count CD4+ T cells using antibody detection methodology is of course dependent on the "signal generation" yield and signal-to-noise expectation (and equipment for data interpretation). For example, fluorescent signal generation is generally associated with lower backgrounds giving better detection of a given target molecule due to improved signal-to-noise ratio (versus a colorimetric approach). In this proposal, we focus exclusively on colorimetric detection as we wish the final test to be low in cost and the operator can see the results as they develop. The most inexpensive and common reagent to employ in an ELISA reaction, which generates a colorimetric endpoint, is Alkaline Phosphatase (AP) using BCIP/NBT as substrate. We demonstrate that this approach is capable of producing appropriate results without expensive conjugates such as nano-gold.

Attribute 4.

The assay must be substantially free of existing intellectual property constraints. Approach: An overriding principle in our current design of the CD4 assay is that as designed, it is composed of methods and compositions which avoid proprietary processes and compositions, i.e. the methods and compositions we have devised are already in the public domain. We reasoned that if we employed only technologies that we knew were either unencumbered or had passed the twenty-year barrier from the time of patent issuance (i.e. explicitly in the public domain by both U.S. and international patent law), uncontrolled costs due to licensing could be avoided. For example, with respect to the use of immuno-chromatographic strips (nitrocellulose, etc.), a fair number of public domain patents (c.f. Gould et al., 1985; Tom et al., 1982; Deustch and Mead, 1978; Valkirs et al., 1986 and references therein) exist, which make it clear that the general process is free from intellectual property constraints. Similarly, ink jet deposition of biological materials (antibody, DNA, etc.) has also existed for a surprisingly long period of time and analysis of expired patents (c.f. Johnson, 1980; Sangiovanni and Michaud, 1982; and references therein) reveals that simple ink-jet deposition of biomolecules onto a substrate does not appear to be IP-constrained. Other required steps are also in the public domain. For example, we need to conjugate oligonucleotides to antibodies to construct the avidity reagents and this chemistry has been known for decades (Smith, 1976; Batz et al., 1981). The decision to use colorimetric (BCIP/NBT) detection was also driven by consideration of cost, as many of the dyes in current assays are proprietary (for example the vast majority of Invitrogen Corporation, aka Molecular Probes, dyes are quite expensive and require a license for commercial use), although aside from the costs they would be useful and suitable for the assays. As far as the avidity constructs are concerned we will employ a linear polynucleotide approach that we developed previously as a signal amplification scheme (Lane et al., 1999, 2001), which yielded a greater than $10^3$ fold amplification signal (Lane et al., 1999, 2001). For the purpose of the CD4 assay it is important to understand that 1) these prior patents are to methods and kits using the amplification method (not composition claims to the DNA structures) and 2) these two patents were awarded subject to a file wrapper estoppel requiring that the homogeneous polymer (e.g. polyd(A)) be greater in length than 3000 nucleotides.

Business Potential

In the developed world, flow cytometry is the available gold standard and there is little impetus for changing this. In the underdeveloped world, this option is not only unaffordable but also requires a high degree of technical sophistication. CD4 counting assays that have been designed to fill this need, while certainly more affordable than flow cytometry, still require either equipment and/or technical sophistication to perform. From this perspective, the argument could be made that there is very little profit motive to develop and market such tests. In fact, some larger corporations have withdrawn CD4 count tests from the market (c.f. Zymmune and TRAxCD4). First world requirements for approval of new diagnostic tests present an additional monetary barrier for corporations, which, for all practical purposes, must show either a profit or the potential for it. Yet, if the pricing scheme for such a test is not as low as possible, the test will not be deployed where it is most needed. We believe that we can demonstrate that such a test can be made in such a way as to be free of costly licensing issues. Furthermore, it can be manufactured locally, if the assay is designed with the appropriate attributes. We also believe that demonstration of our ability to design and construct such a test would generate first world interest in the avidity-based lateral flow strategy.

Design of Assay and Detection Scheme

Figure 2:
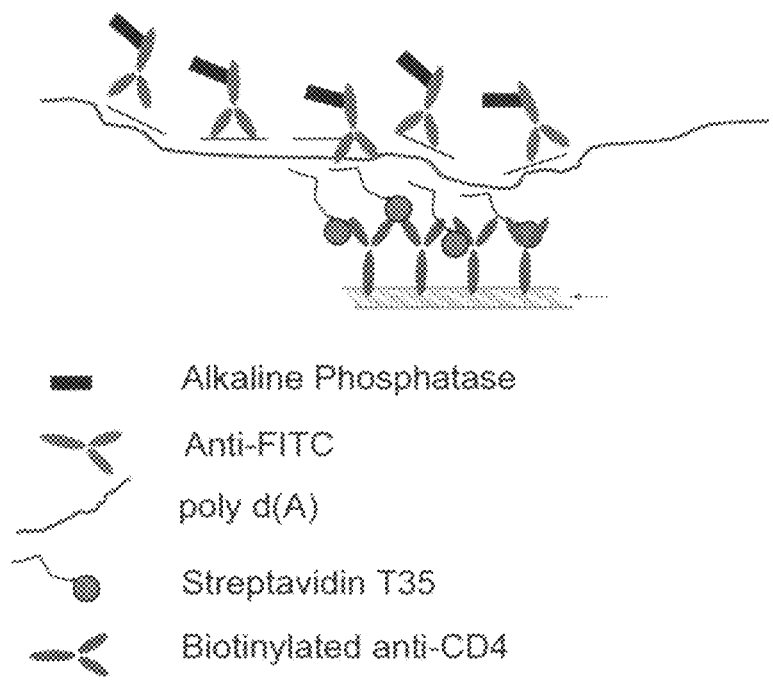
FIG. 2. Schematic depiction of testing Streptavidin-d(T)35 conjugate.
Figure 3:
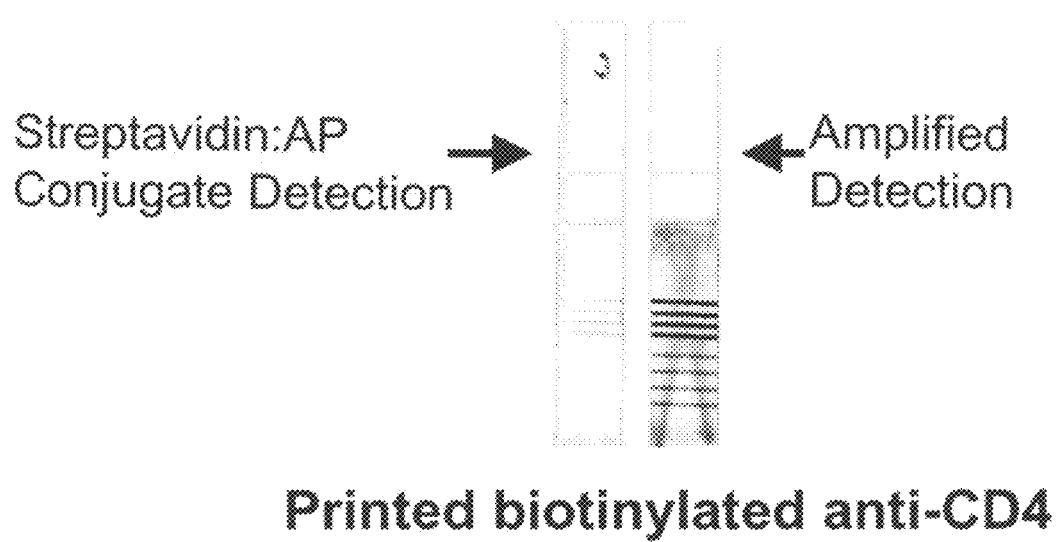
FIG. 3. Demonstration of Streptavidin:dT35 conjugate viability using polyd(A) based linear amplification vs. Streptavidin:AP conjugate direct detection. Two identical strips were prepared as follows; four lines of two concentrations of biotinylated anti-CD4 antibody was printed (at 10 ng/ml and 1 ng/ml) using an HP inkjet printer. The strips were blocked in 0.5% cassein for 20 min. followed by addition of a wicking pad. For the amplification test using the Streptavidin:d(T)35 conjugate the next step was to wick 100 ul TBS (wash step) followed by 100 ul of Strept-T35 at 0.057 pmoles/ul in TBS; next another 100 ul TBS wash step followed by 100 ul of polyd(A) at 430 pgrams/ul in TBS; next another 100 ul TBS wash followed by 100 ul of a dT20-FITC oligonucleotide at 0.1 pmoles/ul in TBS followed by a wash stop of 100 ul TBS; next 100 ul mouse anti-FITC:AP conjugate at 0.067 pmoles/ul in TBS followed by a 100 ul TBS wash and finally addition of BCIP/NBT to produce signal for 10 min. at RT. Reaction was stopped by addition of 10 ul proteinase K at 0.1 mg/ml. The control strip received a wash step for all reagent addition steps and was developed with 100 ul of Streptavidin: AP conjugate at 2.1 pgram/ul followed by a wash with 100 ul TBS and development with BCIP/NBT.

Our initial design for capture and detection of CD2+ CD4+ T cells involved "printing" anti-CD2 "bands" to capture the T cells, followed by introducing biotinylated anti-CD4 to label the bound cells, followed by use of streptavidin: alkaline phosphatase and BCIP/NBT substrate to generate signal. The ability to count CD4+ T cells using antibody detection methodology is of course dependent on the "signal generation" yield and signal-to-noise expectation. The most inexpensive and common reagent to employ in an ELISA reaction, which generates a colorimetric endpoint, is Alkaline Phosphatase (AP) using BCIP/NBT as substrate. Given this constraint, the question arises: Can the colorimetric approach be reasonably expected to produce a visually observable signal at the levels of CD4 cells relevant to the problem? The answer comes down to assessing both the number of AP molecules necessary to generate detectable signal (detection limit) and the number of CD4 receptors which an anti-CD4:AP conjugate would be expected to encounter at the requisite CD4 cell counts for the assay. Preliminary results spotting AP on the nitrocellulose substrate we are currently using generates a detection limit of ~$10^9$ copies of AP (signal generation after 15 minutes at room temperature in a 1 square millimeter area—data not shown). Human CD4+ cells average ~$10^5$ copies of the CD4 receptors per cell (Lenkei and Andersson, 1995), and using these values we can determine whether a colorimetric approach is feasible. The CD4 "counting" levels necessary are minimally 250 cells/uL and working from a 100 uL sample this would yield $2.5 \times 10^9$ copies of CD4 available for binding, which is sufficient to produce a visible colorimetric signal even at the 250 cells/mm$^3$ level, albeit close to the detection limit. To augment this signal we have employed a robust non-enzymatic means to amplify the result up to several hundred-fold (Lane et al., 1997, 2001) to aid in routine visualization. Our approach is shown schematically in FIG. 2 and the experimental implementation of this signal amplification process is shown in FIG. 3. We characterized the amplification by printing biotinylated anti-CD4 onto test strips and measuring the degree of signal amplification we could obtain after 1) running 100 uL of various dilutions of streptavidin-T$_{35}$ over the strip followed by 2) hybridizing polyd(A) to the printed antibody:conjugate complex followed by 3) hybridization of a T20-FITC conjugate oligonucleotide and 4) monitoring the reaction colorimetrically using an anti-FITC:AP antibody followed by BCIP/NBT detection.

Test Strip Assembly Process

Figure 4:
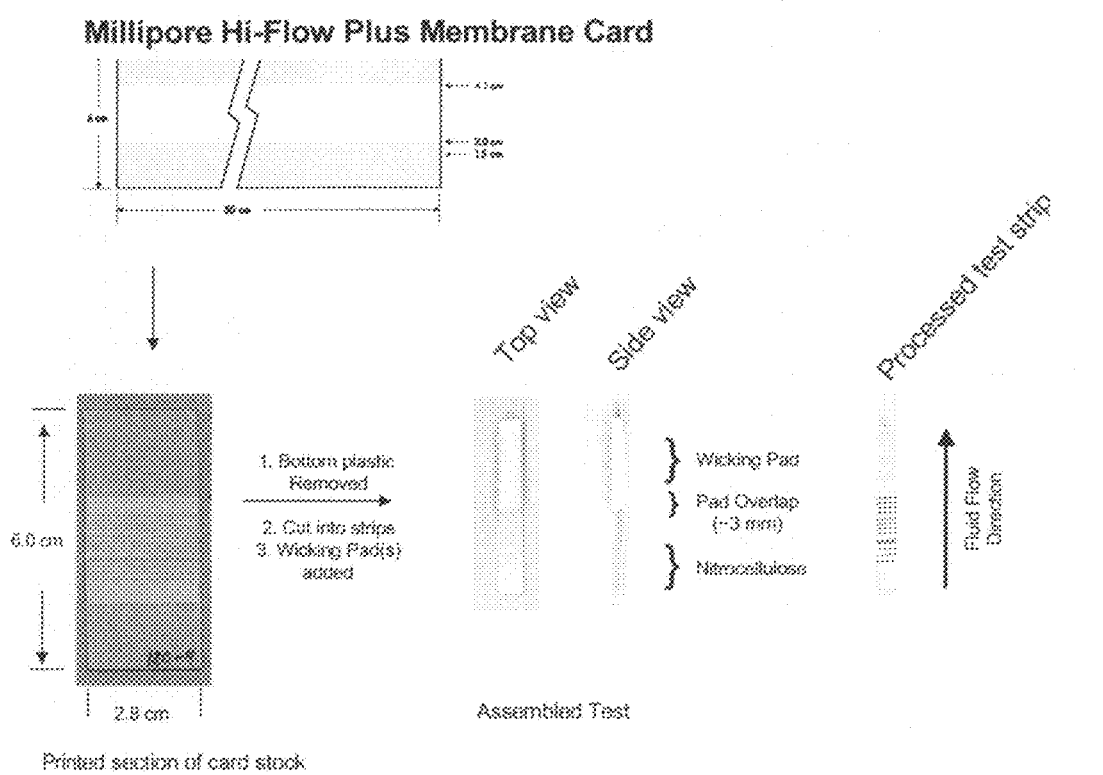
FIG. 4. Assembly steps for inkjet printed lateral flow assay.
Figure 5:
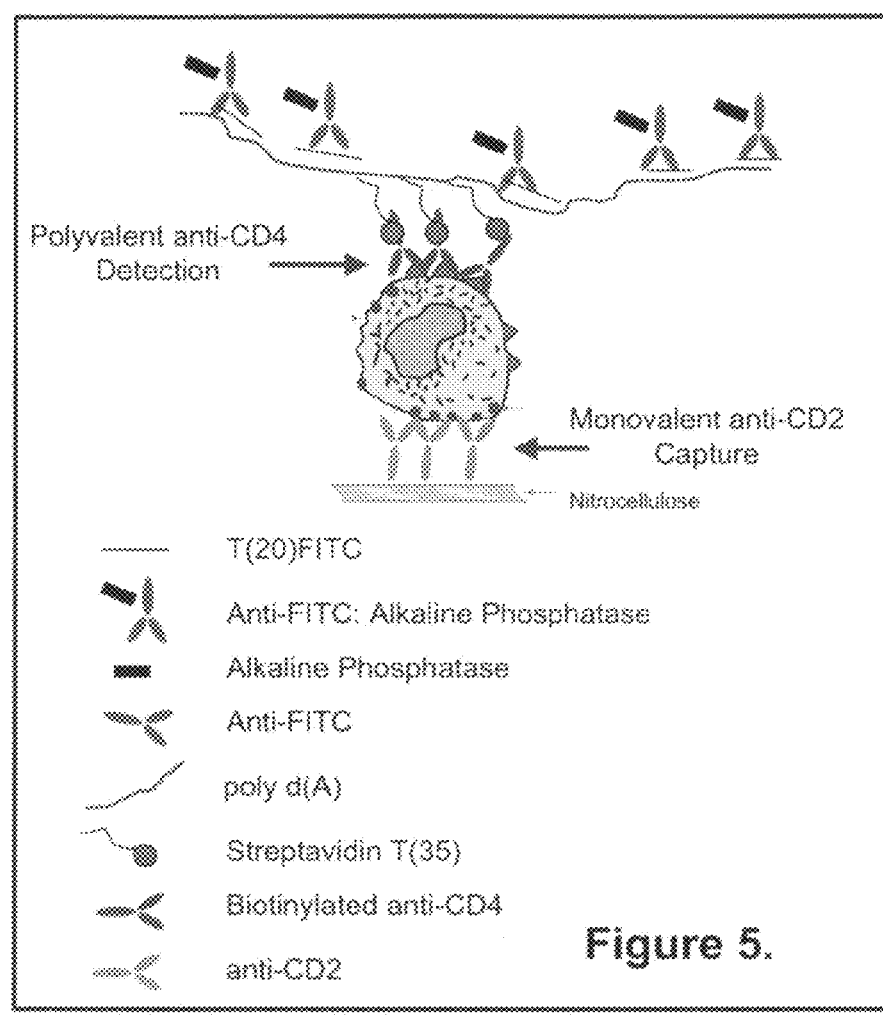
FIG. 5. Schema of CD4+ T cell detection strategy.

Before discussing the designs for the CD4+ counting assay, the steps involved in assembling test strips are summarized (see FIG. 4). In brief, Millipore lateral flow card stock is cut to desired size (i.e. depending on number of test strips desired), taped to 8.5×11 in. paper, and, antibody printed onto the card stock. Printing involves opening an HP27 (or HP28 color) print cartridge, removing the ink and foam, followed by rinsing extensively with water. Then the "screen" over the printhead is removed carefully with tweezers. The print cartridge is extensively rinsed again with water followed by printing distilled water continuously over an entire page to "purge" the printhead of any remaining ink residue. Then 100 uL of antibody/protein solution is added (spiked with yellow food dye to monitor printing). Any pattern may be constructed in a graphics package (we used Microsoft Powerpoint). After printing, the cartridge is rinsed with water and purged by printing a page with distilled water. The cartridges can be used repeatedly if washed appropriately after each use. The printed card stock is then cut into 5 mm "strips", after removing the plastic from the "nonwick" side of the cut strip. A "wicking pad" is attached such that it overlaps the nitrocellulose by ~2-3 mm.

Search for a Membrane(s) that Would Support T Cell "Lateral Flow"

We initially assumed that the ability of T cells to flow into a membrane in a rapid test format would not be technically problematic. As we started exploring the movement of cultured T cells in membranes, it became clear that this was not the case. We employed a variety of membranes to test T cell flow of cultured cells. First, we found that if a strip was used in a vertical format, as we originally envisioned, the cells did not move into the membrane, while the fluid "wicked" up through the membrane. This prompted us to attempt placing the cells by pipette onto the surface of the nitrocellulose. Again no cell movement was detected on any membrane. This included a membrane made by Porex Corp. with reported pore size roughly equivalent to the expected 10 um diameter of a T cell.

We next tried placing a 100 uL "bead" of cell suspension on a hydrophobic surface (using a 24 well plate cover) and "sliding" a pre-wetted nitrocellulose strip into the bead. The idea behind this approach was that when one watches fluid flow across a nitrocellulose membrane there is visible liquid flow across the surface. We reasoned that if the membrane was saturated with buffer when the cells were introduced then we could avoid "absorption" of the cells by the membrane and the cells might "bounce" along the surface (and could be caught by a surface printed antibody). This produced a dramatic change in the response of the cells as the entire 100 uL, including cells, flowed across the membrane in approximately 30 seconds, as long as it had been pre-wetted. We were able to produce this effect with two commercial plastic-backed membranes, Millipore 065 and 075. The results are summarized in the Table 2. At present we are carefully pipetting cells/blood onto the membrane in 10-15 uL aliquots after the membrane is pre-wetted which accomplishes the same objective (pre-wetting the membrane is the critical step).

TABLE 2

Summary of Membrane Studies

| Membrane Designation Manufacturer | Membrane Type | Flow Rate-100 uL (~sec/2.5 cm) | Inkjet Printable | Supports Non-Cellular Lateral Flow | T-cell Capable |
|---|---|---|---|---|---|
| Millipore 180 | Nitrocellulose | 861 +/− 29 | Yes | Yes | No |
| Millipore 075 | Nitrocellulose | 242 +/− 17 | Yes | Yes | Yes |
| Millipore 065 | Nitrocellulose | 242 +/− 17 | Yes | Yes | Yes |
| GE Osmolab 5.0 | Nitrocellulose | 2053 +/− 154 | Yes | Yes | No |
| GE Osmolab 8.0 | Nitrocellulose | 1608 +/− 490 | Yes | Yes | No |
| GE Osmolab 1.2 | Nitrocellulose | 1686 +/− 88 | Yes | Yes | No |
| Porex | Polyethylene | 233 +/− 41 | Yes | Yes | No |

T Cells which "Flow Over" the Pre-Wetted Membrane can be Bound by a Printed Anti-CD2 Capture Antibody Followed by Anti-CD4 Detection (First CD4 Cell Capture Iteration).

Figure 6:
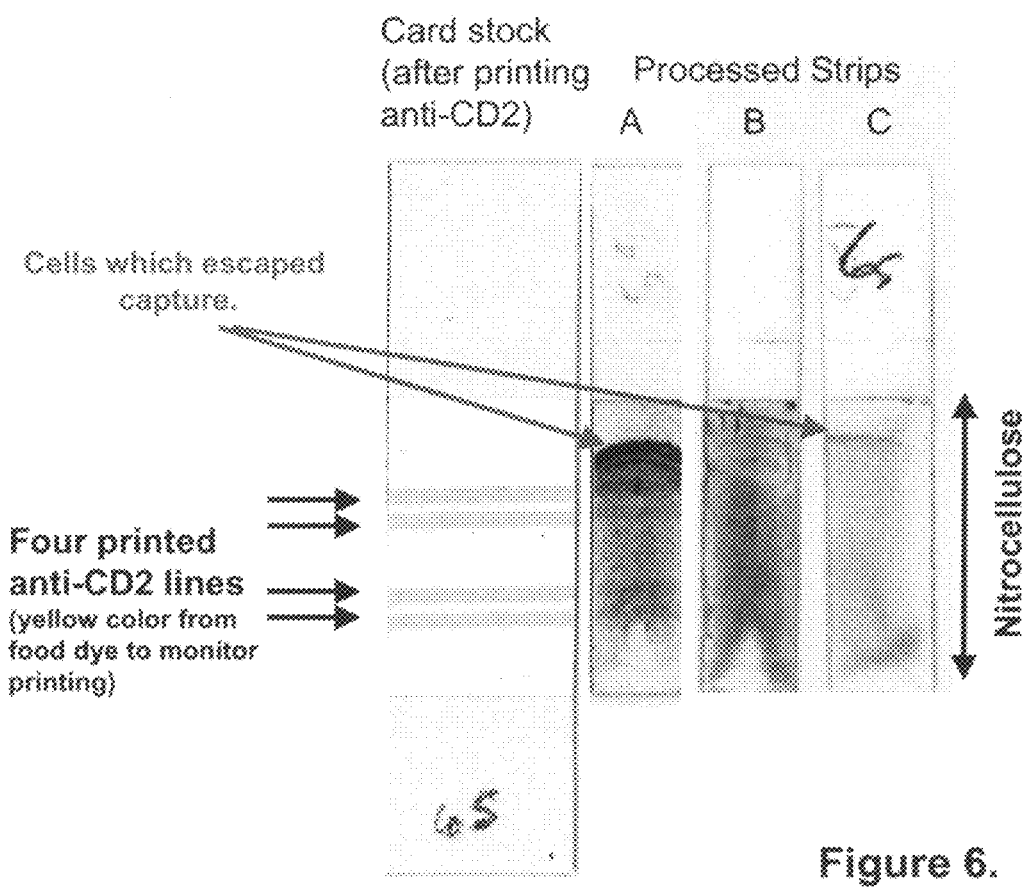
FIG. 6. T cells can be detected on an immunochromatographic strip. Strip A demonstrates detection of T cells. Strip B was processed identically to A except no cells were used (minus cell control). Strip C served as a "direct detection" (e.g. without enhanced detection steps). Briefly. CD4+ Jurkat T lymphoma cells (CD2+, CD4+, ATCC TIB-152) [maintained in RPMI 1640 with 10% heat-inactivated fetal calf serum, penicillin (100 U/ml), streptomycin (100 U/ml), L-glutamine (2 mM), and 50 uM b-mercaptoethanol] were used as the target cells to demonstrate cell capture. Cells for the experiment were at ~3×10$^6$ /mL initially and kept in media. A 100 ulL aliquot was supplemented with 20 ug biotinylated anti-CD4 mAB until 10 minutes before use when 10 uL of 0.5M EDTA (pH=8.0) was added to 90 uL of the cell suspension (containing ~3×10$^5$ total cells/mL or 3000 cells/uL. Test "strips" were processed as follows: 1) One third of a Millipore 065 nitrocellulose membrane card was taped to paper and 2) four antibody lines were then "printed" onto the nitrocellulose by introducing anti-CD2 mAB into a type 27 HP print cartridge and using a pre-generated powerpoint file; 3) a ~5 mm "strips" were cut from the printed membrane card and pretreated in 0.5% Casein "blocking" solution for 30 min. After this a "wick" was added to one end of the strip and 100 uL 1×TBS rinse was allowed to flow vertically across the membrane into the wick. Processed strips: A. This strip was place horizontally and buffer was placed on the stripto prewet it. Then 100 uL of cells (CD2+, CD4+) was carefully pipetted in ~15 uL aliquots such that the nitrocellulose remained wet throughout the process. B. This strip was a minus cell control where 100 ul TBS was added in the same fashion as A. C: This strip received cells identically to A. Immediately following the cell solution traversing the membranes the strips were placed into a well containing 100 uL TBS wash which was wicked vertically up the membrane. Next strip C received 100 ul Streptavidin:AP conjugate at 2.1 ngram/ml, a wash and BCIP/NBT was used to develop signal. A and B: Next, 100 uL of streptavidin d(T)35 conjugate at a concentration of 0.05 pMoles/ul in TBS was added and wicked across the membrane followed by a 100 uL TBS wash. Next, 100 uL of poly d(A) solution (Sigma) at a concentration 0.43 ng/uL was wicked up the membrane to bind the bound cells followed again by a 100 uL TBS wash step. Signal was generated by allowing 100 uL of FITC d(T)20 conjugate to wick up the membrane followed by a 100 uL TBS wash step. This was followed by 100 uL of an anti-FITC: alkaline phosphatase conjugate at a concentration of 0.0670 pmoles/uL and BCIP for signal generation (~40 min.).

To test whether or not the lateral "flow over" approach was suited to actual capture of T cells by ink-jet printed antibody, anti-CD2 was printed to the nitrocellulose in the pattern shown in FIG. 6 and Jurkat cells (CD2+, CD4+) were allowed to flow over pre-wetted test strips. In this experiment, all steps except the addition of cells were conducted with the test strip in a vertical position (i.e. a "flow-through" configuration). Two controls were employed, a minus cell control and a direct detection control. This same experimental format was also conducted using other membranes as listed in Table 2. We found that, at least with our current protocols, both the Millipore 065 membrane and the Millipore 075 membrane performed satisfactorily, as there was a signal indicating bound CD4+ T cells. Both of these membranes are used in the current assay and available readily.

Redesign of Strip Architecture to Account for the "Flow Over" Method of Moving Cells on the Nitrocellulose.

Figure 7:
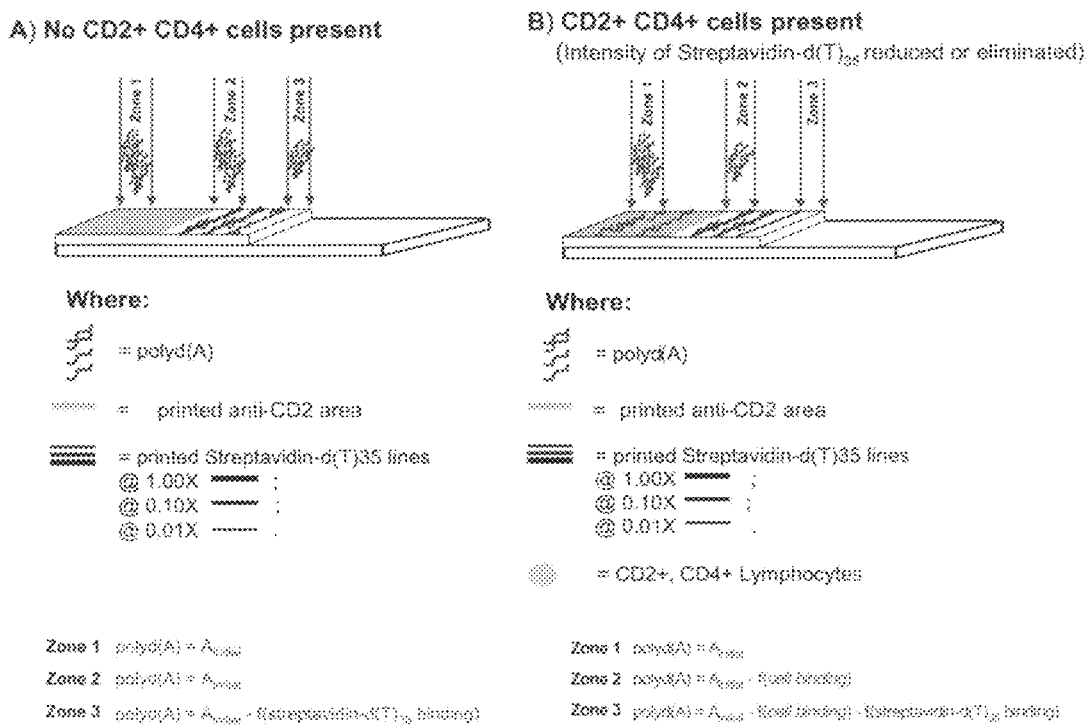
FIG. 7. Depiction of redesigned CD4 assay. Indirect assay for CD2+ CD4+ cells. Anti-CD2 printed area is depicted in blue, streptavidin-d(T)35 lines in black. Polyd(A) molecules are represented as blue squiggles. Flow proceeds from zone 1 through zone 3. A) If no CD2+ CD4+ cells (represented by red dots) are bound to the anti-CD2+ area then any polyd(A) introduced simply flows through the membrane and is bound by the streptavidin-d(T)35 printed lines to an extent governed by the polyd(A): streptavidin-d(T)$_{35}$ equilibrium constant. B) If T cells have been introduced and are present on the anti-CD2 lines then (by virtue of the presence of biotinylated anti-CD4: streptavidin-d(T)$_{35}$ complex bound to the T cell CD4 receptor) the cells bind a fraction of the polyd(A) as it flows up the strip. In this situation the observed binding of polyd(A) to the streptavidin-d(T)35 lines further up the strip show diminished (or eliminated) polyd(A) binding (governed by the polyd(A): streptavidin-d(T)$_{35}$ equilibrium constant), resulting in the "disappearance" of lines with increasing T cell content. "Zones" of polyd(A) "concentration" are shown with equations for polyd(A) copy number for both cases.

FIG. 6, while demonstrating that printed anti-CD2 can capture cells when applied so that they flow over the top of the membrane, also illustrates that the cell capture process is inefficient as cells "miss" the printed anti-CD2 (note: "Cells which escape capture", see FIG. 6). We attempted to improve the capture efficiency by widening the printed bands; while this improved the situation we could still detect cells that migrated all the way to the pad (using microscopy) in this configuration of the assay. We next attempted to see how well the cells could be captured if we printed anti-CD2 continuously over the first 50% (for reference see FIG. 1) of the nitrocellulose. While this solved the cell capture problem, as evidenced by eliminating T cell flow all the way across the strip, it necessitated a change in how we could count cells. To address this issue we re-engineered the same assay components into a new configuration, which we felt could respond to all captured cells. In essence, we attempted to decrease the area over which the signal was dispersed by measuring the depletion of polyd(A) by CD2+ CD4+ bound cells lower on the strip, using three printed streptavidin-d(T)$_{35}$, polyd(A) capture lines. A cartoon illustration of the approach is given in FIG. 7. In effect, the redesign and improvement uses the polyd(A) as a "surrogate marker" for the presence of CD2+ CD4+ lymphocytes. The advantages of the approach are two-fold: 1) the concentration of all three streptavidin-d(T)$_{35}$ lines can be adjusted (increased or decreased) to increase or decrease the amount of polyd(A) dependent signal generation and 2) the signal generation area is reduced to 2.5-5.0 mm$^2$ which is within the signal generation range for the system (alkaline phosphatase: BCIP/NPT) given the number of expected signaling moieties (e.g. cells). A key consequence to this redesigned assay format is that the presence of a given streptavidin-d(T)$_{35}$ band may be used to indicate a lack of cells sufficient to sequester enough polyd(A) to eliminate a streptavidin-d(T)$_{35}$ line. This means that the interpretation of the results of this assay is different from that in FIG. 6; as more CD2+ CD4+ cells are present in the sample, fewer streptavidin-d(T)$_{35}$ bands will appear, or the band intensities will be diminished relative to a strip that does not receive T cells. In our first iteration of the present redesign assay architecture we performed the assay as a qualitative assay (i.e. interpretable by visible inspection with complete loss of the lowest concentration streptavidin-d(T)$_{35}$ printed band).

The Indirect Detection Assay Design Functions in the Presence of Whole Blood.

Figure 8:
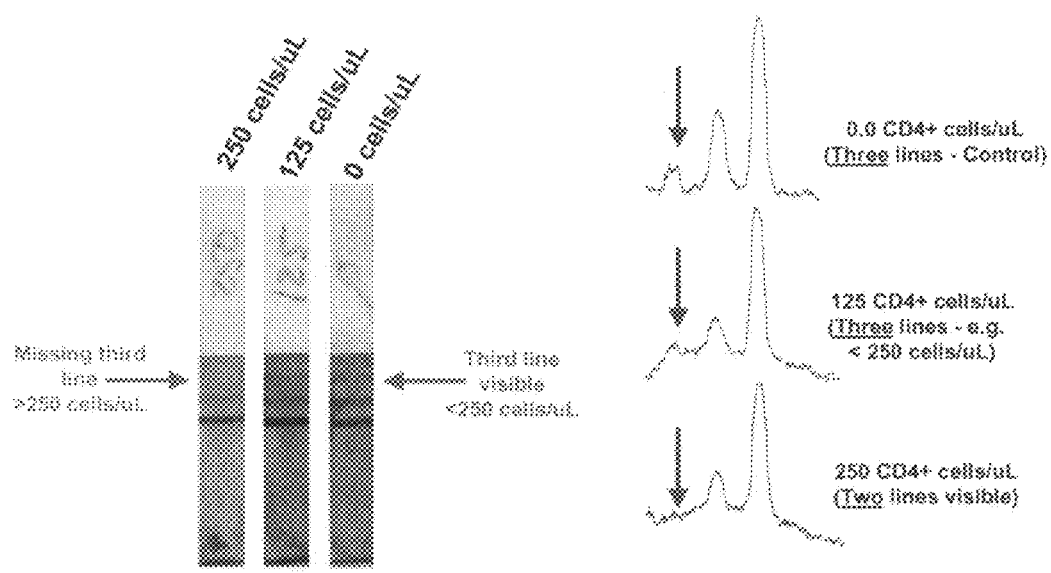
FIG. 8. CD4 counting assay works in fresh blood and can distinguish between 125 cells/uL and 250 cells/uL or greater. Discrimination between 0.0 CD2+, CD4+ and 250 CD2+, CD4+ cells in fresh 1:2 diluted whole chicken blood. On the left are the nitrocellulose strips and on the right densitometric scans of the result are shown. Interpretation: lack of the uppermost streptavidin-d(T)35 line in the 250 cells/uL indicates that T cells trapped on the anti-CD2 portion of the strip sequestered enough polyd(A) to eliminate polyd(A) binding to the uppermost line—therefore CD4+ cells are present at 250 cells/uL or greater. In this assay format if three lines are visible the sample contains <250 cells/uL.

The next step was to demonstrate that the assay could detect human T cells in whole blood. Initial experiments utilizing CD2+ CD4+ T cells "spiked" into whole chicken blood revealed that, with even if as little as 15% of our cell sample (15 uL blood brought to 100 uL), signal was not observable from the streptavidin-d(T)$_{35}$ lines on the strip. We reasoned that non-specific cell or blood detritus bound to the anti-CD2 portion of the strip could cause this. This suggested to us that a "stringent wash" procedure, capable of removing non-specific components but that does not disrupt the anti-CD2: CD2 receptor interaction could allow the system to function. To test this we executed a series of post-cell-addition wash experiments with 1.0-8.0M urea dissolved in PBS. These experiments demonstrated that above 4M urea the signal generation was compromised (probably due to cell lysis) versus no urea control strips (data not shown). As is shown in FIG. 8, inclusion of this 4.0 M stringent wash procedure after blood/T cell introduction to the strip allowed detection of "spiked" CD2+ CD4+ T cells in whole blood. The new assay architecture, while interpretable using scans of the results, was not as robust when we asked lab personnel to actually call the presence or absence of a streptavidin-d(T)$_{35}$ "band" by simply looking at a result as the signal developed over time. Different individuals observing the reaction indicated that they "observed a band" when others would not see the same "band", sometimes until minutes later. This led us to modify our procedures yet again: if students and Ph.D. professionals could not accurately identify the absence or presence of a streptavidin-d(T)$_{35}$, it seemed this approach might not be best suited for untrained personnel. We then modified the assay to truly quantify the number of CD2+ CD4+ T cells in a sample.

Another Iteration of the CD4 Assay: Quantitative Counting Using the CD4+ T Cell Assay Design Architecture.

In the previous experiment, with blood, what was done to achieve the experimental results was to cross-titer polyd(A) concentration versus total cells loaded until we had a result which was low enough in polyd(A) to deplete the third streptavidin-d(T)$_{35}$ band in fifteen minutes (although, as previously mentioned, some observers saw a third "band" under these conditions). In thinking about what we were observing we came up with the notion that perhaps a cell phone photograph series taken over 20-30 minutes could make the assay quantifiable by remotely located trained experts, as such photographs could be emailed directly to the Internet. The photographs could then be used to calculate rates of development of the three streptavidin-d(T)$_{35}$ bands and the results used to calculate the number of CD4+ T cells in a sample. The interpretation could then be emailed back to the user's cell phone.

Figure 9:
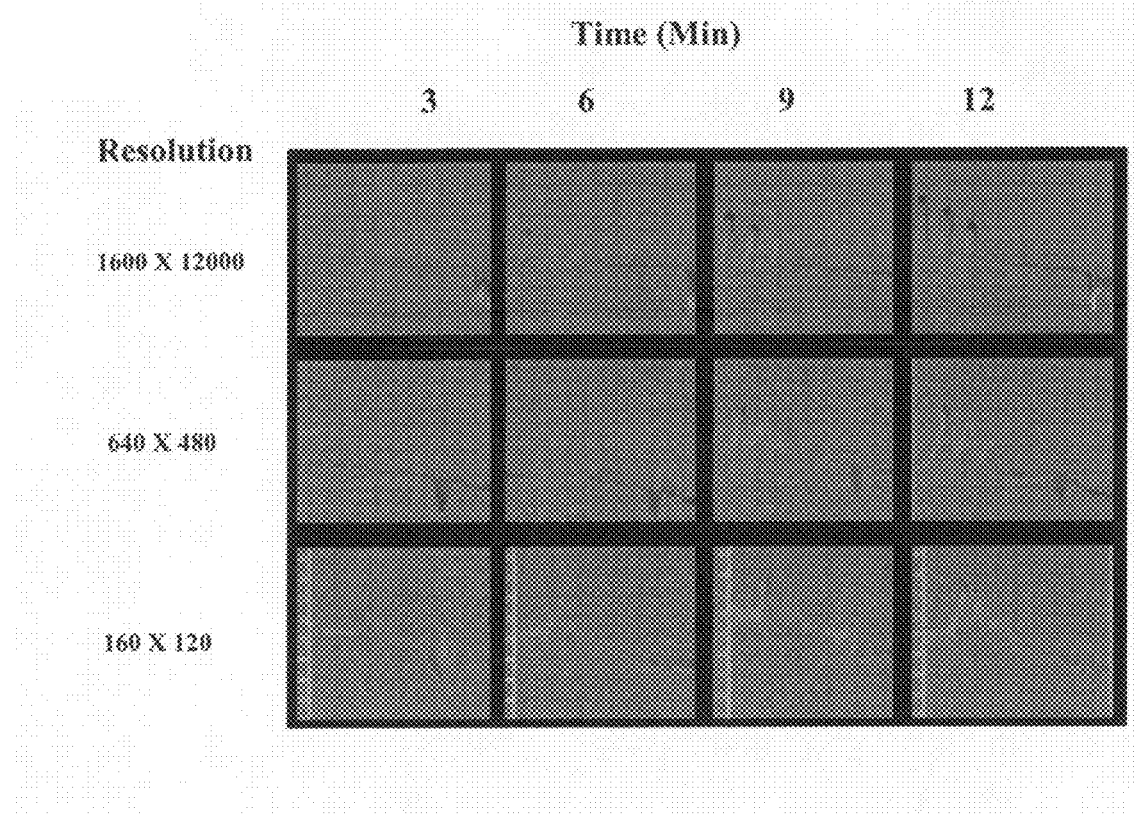
FIG. 9. Examination of cell phone resolutions producing viable data from CD4+ T assay.

To investigate this notion, our first question was: would such a strategy produce useable data versus a high-resolution camera? FIG. 9 is a comparison of the most common standard, high-resolution cell phone picture (1600×1200 pixels), for inexpensive cell phones, and next lowest standard resolution (640×480 pixels). In this lower resolution picture, the rates were dramatically different, as is obvious by visual inspection.

For FIG. 9, the method was as follows: Strips are placed on template, a white sheet of paper with two lines and a dot that were manually drawn, used to normalize between different picture resolutions. BCIP is applied to strip and a timer is started. At 3 minute increments, pictures were taken with cell phone making sure to keep a constant height (6 in.) and keeping cell phone perpendicular to strip. This was repeated for each picture resolution. To normalize possible light issues at each picture resolution, ImageJ (NIH) was used to construct 3D surface plots over manually drawn lines on background template using the surface-plot-3d macro (courtesy Dr. W. Rasband). Using the same size box for all images, place over line and create 3D surface plot. Measure the intensity (peak height) of the line for each of the different resolutions using standard protocol for collecting data. Set highest resolution intensity as one by dividing highest resolution intensity by each of the other resolution intensities. Store resulting quotients to later be used when measuring intensities of Streptavidin-d(T)$_{35}$ lines. For picture size normalization, with each picture taken, resize to a standard picture size using PowerPoint®. To make sure each strip from each picture is the same size, use the dot and lines that were drawn on the background template. By manipulating picture size in PowerPoint make sure that there is the same distance between the two lines in the picture being resized and the resizing template. After resizing, crop unwanted areas of each picture leaving only the nitrocellulose strips. Save each resized picture so they can later be used to collect intensities of streptavidin-d(T)35 lines over time. For each resized picture, intensities were measured of the streptavidin-d(T)$_{35}$ lines using ImageJ 3D surface plots. Before creating the 3D surface plots, the z-scale of the macro is altered to the quotient previously determined when normalizing to light differences. Collect line intensities (peak heights) using standard protocol for collecting data (making sure the same size box is used). This process was repeated for each picture resolution. Conclusion: The first two resolutions employed give essentially identical peak height values but camera resolution must, at minimum, be 640×480 pixels for remote analysis of rates.

Building a Metric for Interpretation of Streptavidin-d(T)$_{35}$ Band Intensities Based on Rate of Signal Development.

In order to better understand the performance of the three streptavidin-d(T)$_{35}$ bands in the presence of cells bound on the anti-CD2 area of the strips, we first studied the signal produced in the absence of cells at varying polyd(A) concentrations (see FIG. 10). A Polyd(A) titration experiment was conducted with Streptavidin-d(T)$_{35}$ bands printed at streptavidin-d(T)35 input concentrations of 57, 28.5 and 14.25 pMoles/uL (Band 1, Band 2, and Band 3 respectively). Strips were then blocked in 0.5% Casein "blocking" solution for 30 min. and wicks added. Next 100 uL of polyd(A) solution (Sigma-Aldrich) was flowed up the membrane followed by a 100 uL PBS rinse. Next, 100 uL of d(T)20-FITC conjugate at 0.03 pMol/uL was flowed up the membrane followed by a 100 uL PBS rinse step. To detect bound d(T)20-FITC 100 uL anti-FITC:alkaline phosphatase conjugate at 0.0023 pMol/uL was flowed up the strip followed by removal of the wick placing the strip horizontal and BCIP/NBT (~100 uL was added to all strips. We standardized the polyd(A) dilution process and "walked down" in polyd(A) concentration by twofold increments. A typical result has been summarized in FIG. 10. This Figure illustrates that the three streptavidin-d(T)$_{35}$ bands perform differently, as expected, at each polyd(A) concentration. In FIG. 10C the intensity increase over time of all three bands for one polyd(A) concentration are shown.

Figure 11:
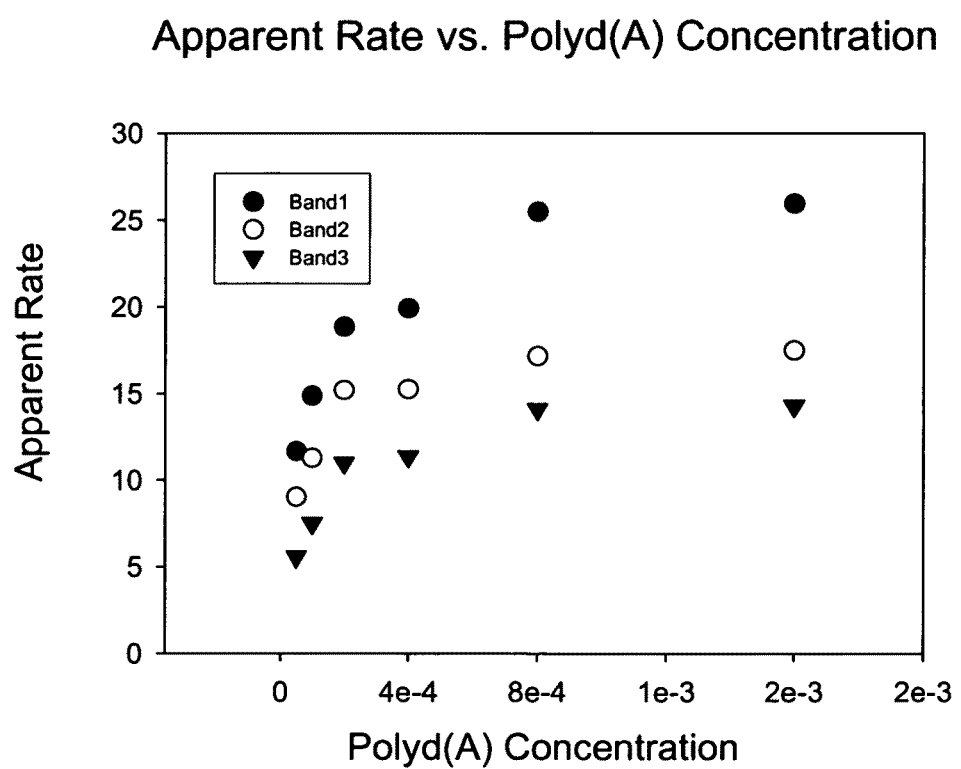
FIG. 11. Rates for each concentration of polyd(A) and for each streptavidin-d(T)$_{35}$ band. At all concentrations of polyd (A) the three bands give distinct rates (see text).

The entire system acts as a zero order reaction but all three bands give saturation behavior that "saturates" at lower peak levels for lower printed streptavidin-d(T)$_{35}$ concentration bands in the current configuration (i.e. less polyd(A) can be hybridized to the lower concentration streptavidin-d(T)$_{35}$ printed bands). Given that the observed performance of the intensity increases for all bands versus time we next calculated rates using linear least square fits to the intensity data staying below 60% of the saturation values. This strategy gave excellent $r^2$ values for all polyd(A) concentrations ($r^2 \geq 0.95$) indicating excellent linear fits. These rates are summarized in FIG. 11.

The utility of collecting this information is briefly summarized here. We reasoned, that understanding the rate behavior of the system in the absence of CD2+ CD4+ cells would allow us to calculate the number of polyd(A) molecules bound to the T cells. The presence of T cells on the printed anti-CD2 area (see FIG. 1) depletes polyd(A) from the input polyd(A) to the system and when this happens the rate reduction can be compared to the T cell dependent loss of streptavidin-d(T)$_{35}$ band intensity. This information can be used to estimate the total reduction in polyd(A) concentration caused by the T cells.

the T Cell Assay Shows Dramatic Depletion of Polyd(A) Signal as a Function of the Number of T Cells Introduced.

Based on the data above we set out to see how the streptavidin-d(T)$_{35}$ bands responded to the introduction of T cells of using a polyd(A) concentration of 0.43 nanograms/100 uL. This concentration corresponds to the second strip from the right in FIG. 10A above. The results of this experiment are shown in FIG. 12. The expectation of diminished streptavidin-d(T)$_{35}$ band intensities suggested that a longer time collection period was needed and therefore we doubled our data collection time from 20 minutes, as in the polyd(A) experiment above, to forty minutes, over which time one picture was taken every minute. The forty-minute time point for all strips is shown in FIG. 12A. What is obvious is that even with as few as 31.5 CD2+ CD4+ T cells/uL (100 uL cell volume yielding a total 3150 T cells added to this strip) there is visible band intensity loss in the three streptavidin-d(T)$_{35}$ bands versus the control which received no cells. Scans of the strips shown in 12A are presented in 12B. Comparison of the control with the 31.5 T cell/uL scan confirms the visual conclusion from simple examination of the strips. Scans for all strips at all time points were analyzed and peak heights used to generate rates for the three streptavidin-d(T)$_{35}$ bands by linear least squares ($r^2$ values for all rates >0.95). This data is summarized in FIG. 12C. Note: The ability to use T cells at 31.5 cells/uL successfully, suggests to us that as little as 15 uL (but no more than 30 uL) of fingerstick blood could suffice in the final assay.

Research Design and Methods

We have demonstrated that the lateral flow assay that we have developed is both specific for CD4+ T cell detection and sensitive enough to detect CD4+ T cells at low levels. We have also shown that this assay can be performed in whole blood. We will continue to optimize the production, use, and quantification steps in using the assay, to demonstrate that the assay can accurately determine CD4+ counts in whole human blood, and to refine and perfect data acquisition and remote analysis protocols using cell phones to acquire and transmit data, with remote analysis of the data for CD4+ cell counts.

Standardize/Optimize all aspects of the prototype test: procedures, reagents, and materials employed. This involves evaluating and optimizing all of the reagents including, different lots of nitrocellulose, anti-CD4, anti-CD2, polydeoxyadenosine (polydA), $d(T)_{20}$ FITC (T20-FITC), anti-FITC: alkaline phosphatase conjugate (FITC:AP) and Streptavidin-$d(T)_{35}$ (StrepT35). These experiments are performed with both CD2+ CD4+ Jurkat cells and human blood. The experiments also allow definition of quality control (QC) metrics to be employed when new lots of reagents are required for the assay. We examine the use of anti-CD3 as the capture antibody because use of anti-CD3 as opposed to anti-CD2 may prevent competition from CD2+ B cells in human blood. These studies further allow definition of quality control (QC) metrics to be employed when new lots of reagents are required for the assay. This involves continuous cross titering of all reagents, generation of a large number of replicate known sample dilutions (to avoid day-to-day experimental variation) and refinement of all data acquisition protocols to provide a robust, highly reproducible assay with a CV of less than 3%.

The Current CD4+ T Cell Counting Assay Steps:

Individual 5 mm nitrocellulose strips, pre-printed with anti-CD2 and three streptavidin-$d(T)_{35}$ dilution bands, are blocked in 5% casein in PBS for 30 min. During the blocking step, the test sample is prepared for assay by diluting 100 µl blood or cells 1:2 in PBS. Then 1.0 uL (0.25 ug) of biotinylated anti-CD4 (eBioscience clone: RPA-T4 (Cat #13-0049)) is added to each 100 uL cell sample, mixed by gentle shaking and incubated for 15 minutes at room temperature. Next, 1.0 uL of streptavidin-$d(T)_{35}$ (57 pmol) is added and the cell suspension is incubated for an additional 15 minutes. 1 min prior to assay, 1.5 uL EDTA 0.5M EDTA (pH 8.0) is added to the cell sample to break up any clumped cells. The test strips are removed from the casein block and precut wicking pads (Millipore "Surewick" celluLose pads (Cat #SA3J071V04)) are attached. A 100 uL PBS wash is flowed up the strips to remove excess casein blocking agent and then the strip is placed horizontally, pre-wetted with 100 uL PBS and the cell sample is added at the base of the strip, 10-15 uL at a time. The cells are incubated on the test strip for one minute after all cells are added, and then 100 uL of 4.0M urea in PBS is "flushed" over the horizontal strip (~45 sec.). While still horizontal the strip is "flushed" 4× with PBS. The strip is then placed vertically into a well of a 24 well containing 100 uL polyd(A) at the desired dilution (stock polyd(A) is currently 430 ng/uL (Sigma P-0887)), which is wicked up the strip. Following a 100 uL PBS wash, 100 uL $T_{20}$-FITC (10 pMole) is wicked up the strip. After another 100 uL PBS wash, 100 uL of anti-FITC alkaline phosphatase (1:40 dilution, Sigma A1812), is wicked up the strip. After a final 100 uL PBS wash, the wicking pads are removed the strips placed horizontally and a "bead" of BCIP/NBT substrate, sufficient to span the entire nitrocellulose area is added. Color development is monitored every minute for 40 minutes using a digital camera with picture taken through the BCIP/NBT. After 40 min. the reaction is stopped by rinsing the strip in distilled water, followed by the addition of 100 uL Proteinase K (1 ug/mL in PBS) in PBS.

Studies to Standardize and Optimize the Current CD4+ T Cell Counting Assay Steps:

Each of the steps of the assay are optimized, from preparation and storage of all reagents, printing of reagents onto nitrocellulose strips, size of strips, preparation, handling, and dilution of blood cell samples, labeling of the CD4+ T cells, to the T cell capture and detection/quantification steps. We will carefully test a range of all reagent concentrations, and incubation times and conditions, starting with the labeling steps using biotinylated anti-CD4 and streptavidin-d(T)35. We will vary and test the amount of anti-CD2+ antibody printed to the strips in the cell capture zone to optimize cell capture. The concentrations and quantities of the detection and readout reagents, the polyd(A), $dT_{20}$-FITC and anti-FITC:AP, etc., will all be varied and tested. Once the optimal dilutions are determined all reagents will be pre-diluted in large volume and aliquoted to control for day-to-day and week-to-week variation in assay results. The amounts of whole blood used for the assay will be varied and optimized. CD4+ Jurkat T lymphoma cells (CD2+, CD4+, ATCC TIB-152), will be used in assay optimization.

Demonstrate that the Quantitative Lateral Flow Assay Accurately Enumerates CD4+ T Cell in Human Blood.

CD4+ T cell numbers in whole blood samples are determined using the lateral flow assay and compared with numbers obtained by standard flow cytometric methods. We have successfully demonstrated that the lateral flow assay that we have developed is both specific for CD4+ T cell detection and sensitive enough to detect CD4+ T cells at low levels, and that this assay can be performed in whole blood. CD4+ T cell numbers in whole blood samples submitted to a laboratory for lymphocyte subset determination are tested using this assay and compared with CD4+ T cell numbers obtained independently by standard flow cytometric methods, e.g. conducted by laboratory technicians.

Since we do not know the CD4+ T cell level prior to testing, we will assume that most of the samples will likely be in the higher range for CD4+ T cells (up to approximately 1000-1100 cells mm3). At this cell number, 2 two-fold dilutions should dilute the sample to a value which give good streptavidin-$d(T)_{35}$ band intensities, i.e. within the response range of current sensitivity of the lateral flow assay. Since the actual cell number may be lower, both cell dilutions will be tested.

The results from the lateral flow CD4+ T cell assay and flow cytometry are subjected to statistical analysis. Correlation coefficients are obtained for the total CD4 T-lymphocyte count for the two techniques. A P value of <0.05 is considered statistically significant. In addition, the coefficient of variation (CV %) is calculated for the separate sets of 10 CD4 T-lymphocyte counts obtained for each method in the reproducibility test. SPSS software and Microsoft Excel is used for data analysis.

Since we have no information regarding the clinical status of the patients prior to testing with the CD4 lateral flow assay, we expect that the CD4+ T cell values for these patients will be wide-ranging. The normal range of CD4+ T cell levels in humans is estimated to be between 450 and 1100 cells/$mm^3$. The assay is tested in its current configuration to determine whether the samples have at least 500 or greater CD4+ T cells.

Complete Refinement of the Data Acquisition and Remote Analysis Protocols.

This aspect includes testing and standardization of the picture quality required from a cell phone, and design of both spatial and light intensity standards to be included with all photographs. In addition, the optimal times for, and numbers of, photographs to be taken for the remote analysis, are determined. The algorithms/procedures used to count the CD4+ cells using the data from the time series of the assay readout lines are also optimized and standardized.

Optimization of the Cell Phone Data Acquisition and Analysis Protocols

Current Protocols

Image Acquisition:

1. Strips are placed on a background template consisting of a white sheet of paper with two lines and a dot; these are used to normalize between different picture resolutions. 2. Final BCIP reagent is applied to strip. 3. At 3 minute intervals, cell phone pictures taken, at constant height and with the plane of the cell phone parallel to strip at all times. 4. Steps repeated for each photo resolution to be tested.

Normalizing to Light and Resolution Differences:

1. For each picture resolution, ImageJ 3D surface plot analyses performed on the standardization lines on background paper/template. ImageJ 3D surface plot analyses then performed on the three streptavidin-d(T)$_{35}$ bands on the strips. 2. Intensities (peak heights) of the lines measured at each of the different resolutions. 3. Normalization between resolutions is performed by setting the highest resolution intensity set to one by dividing highest resolution intensity by each of the other resolution intensities for the template. The resulting normalization quotients are used when measuring intensities of streptavidin-d(T)$_{35}$ bands. (These normalization values are used to set the z-scale of the 3D surface plot ImageJ macro when collecting data.

Normalizing to Different Picture Sizes: 1. Pictures are resized to a standard picture size using PowerPoint. To make sure each strip from each picture is the same size, the dot and lines on background paper are used to adjust the image size. Also, to normalize for pictures that may have been taken at an angle, we determine that the drawn dot on the template is in the same spot of each picture. 2. After resizing, unwanted areas of each picture are cropped, leaving only the nitrocellulose strips in the image. 3. Each resized picture to be saved for later use in collecting intensities of the three streptavidin-d(T)$_{35}$ bands over time.

Collecting Data:

1. For each resized picture, intensities of the streptavidin-d(T)$_{35}$ bands measured using ImageJ 3D surface plots are collected. 2. Before creation of the 3D surface plots, the z-scale is changed to the quotient previously determined when normalizing to light intensity differences. (Each resolution will call for a different z-scale to be used). 3. Streptavidin-d(T)$_{35}$ band intensities (peak heights) are then by drawing a wing-to-wing baseline under the streptavidin-d(T)$_{35}$ bands. 4. Line intensity data saved for rate analysis Using the above, a standardized T cell count dilution metric is constructed onto which the cell phone rate data may be placed to determine the T cell count of the sample.

REFERENCES

Badri M, Maartens G, Mandalia S, Bekker L G, Penrod J R, Platt R W, Wood R, Beck E J (2006) PLoS Med 3(1): e4

Balakrishnan P, Solomon S, Kumarasamy N Mayer K H (2005) Indian J Med Res 121 345-355.

Baradaran, B., Majidi, J., Hassan, Z. M., Abdolalizadeh, J. American Journal of Biochemistry and Biotechnology 1 (4): 189-192, 2005.

Barrett, J (2002) in Gale Encyclopedia of Medicine, December, 2002 by the Gale Group.

Batz, H-G, Horn, J; Stellner, K; Maier, J; Nelboeck-Hochstetter, M; Weimann, G (1981) Hydroxy-succinimide ester compounds. U.S. Pat. No. 4,248,786.

Bendavid, E, Young, S D, Katzenstein, D A, Bayoumi, A M, Sanders, G D, Owens, D K, Arch. Internal Med 168 1910-1918.

Bessos, H, Murphy, W G (2002) "Competitive binding assay immunoassay for platelet antigens in whole blood." U.S. Pat. No. 6,479,246.

Branson B M (2004) Aids Clin Care 16 39.

Branson B M. (2000) Journal of International Association of Physicians in AIDS Care; February:28-30.

Carrière D, Jean Pierre Vendrell, Claude Fontaine, Aline Jansen, Jacques Reynes, Isabelle Pagès, Catherine Holzmann, Michel Laprade, and Bernard Pau (1999). Clin Chem 45: 92-97.

Constantine N T, Kabat W, Zhao R Y (2005) Cell Research 15 870-876.

Constantine, N T and Zink, H (2005) Indian J. Med Res 121 519-538.

Dam T K, Roy R, Das S K, Oscarson S, Brewer C F. (2000) J Biol Chem 275 14223-14230.

Daniak M B, Kumar A, Galaev I Y Mattiasson B. (2006) Proc. Natl. Acad. Sci. USA 103 849-854.

Denny M F, Chandaroy P, Killen P D, Caricchio R, Lewis E E, Richardson B C, Lee K D, Gavalchin J, Kaplan M J. J Immunol. 2006 Feb. 15; 176 (4):2095-104.

Deutsch, Marshall E.; Mead, Louis W. (1985) Test device. U.S. Pat. No. 4,094,647

Glencross D, Scott L E, Jani I V, Barnett D, Janossy G. (2002) Cytometry 50 69-77.

Hackbarth, J S, S-H Lee, X W Meng, B T Vroman, S H Kaufmann, L M Karnitz, Biotechniques 2004; 37 835-9

Imade, G. E., Badung, B. Pam, S., Agbaji, O., Egah, D., Sagay, A. S., Sankalé, J. L., Kapiga, S., Idoko, J., Kanki, P. Clin Diagn Lab Immunol. 2005 January; 12(1): 224-227.

Jacobs E, K. A. Hinson, J. Tolnai and E. Simson (2001) Clin. Chim. Acta 307 49-59.

Jani, I., Janossy, G., Brown D W G and Mandy F. (2002). Lancet Infectious Diseases 2: 35-43

Jani, I., Janossy, G., Iqbal, A., Mhalu, F. S., Lyamuya, E. F., Biberfeld, G., Glencross D. K., Scott L. E., Reilly, J. J., Granger, V. & Barnett, D. (2001) Journal of Immunological methods 257: 145-154.

Johnson, L C. (1980) Method of making printed reagent test devices. U.S. Pat. No. 4,216,245.

Kidd P G; Cheng S C; Paxton H; Landay A; Gelman R (1993) AIDS 7: 933-940.

Kannangai, R., Ramalingam, S., Jesudason, M. V., Vijayakumar, T. S., Abraham, O. C., Zachariah, A., Sridharan, G. (2001). Clin. Diagn. Lab. Immunol. 20 1286-1288.

Khandjian E. W., Biotechnology 5: 165-167, 1987.

Lane, M J.; Benight, A S.; Faldasz, B D. (1999) Signal amplification method. U.S. Pat. No. 5,902,724.

Lane, M J.; Benight, A S.; Faldasz, B D. (2001) Signal amplification method. U.S. Pat. No. 6,245,513 B1.

Lenkei, R. & Andersson, B. (1995) J. Immunol. Methods 183, 267-277.

Liang R, Loebach J, Horan N, Ge M, Thompson C, Yan L, Kahne D. (1997) Biochemistry 94 10554-10559.

Mourez M, Kane R S, Mogridge J, Metallo S, Deschatelets P, Sellman S E, Whitesides G M, Collier R J. (2001) Nature Biotech 19 958-961.

Oroskar, A A (1998) IVD Technol January 11. [Available online at devicelink.com/ivdt/98/01.html.]

Pattanapanyasat K, Thakar M R. (2005) Indian J Med Res 121:539-549.

Pattanapanyasat, K, Hla Shain, Egarit Noulsri, Surada Lerdwana, Charin Thepthai, Varipin Prasertsilpa, Sirirat Likanonsakul, Prakit Yothipitak, Somboon Nookhai, Achara Eksaengsri (2005) Cytometry Part B: Clinical Cytometry 65B 29-36.

Price, K. D., Knupp, C. J., Tatum, A. H., Stoll, M., Jiang, F., Gavalchin, J. (2002). J. Autoimmunity 19(3): 87-101.

Sangiovanni, J J.; Michaud, R J. (1982) Ballistically controlled nonpolar droplet dispensing method and apparatus. U.S. Pat. No. 4,341,310.

Smith (1976) Compound, dithiobis-(succinimidyl propionate). U.S. Pat. No. 3,940,420.

Tom, H K.; Rowley, G L. (1982) Concentrating zone method in heterogeneous immunoassays. U.S. Pat. No. 4,366,241.

Valkirs G E, Owen C E, Levinson P A (1986) Method and Apparatus for Immunoassays. U.S. Pat. No. 4,632,901.

von Lode P (2005) Clin Biochem 38 591-606.

Weiss, A. (1999) IVD Technol November/December 42. [Available online: devicelink.com/ivdt/archive/99/11/009.html]

World Health Organization (2005) 3 by 5 progress report: Available who.int/3by5/.

Zeytinoglu A, Turhan A, Altuglu I, Bilgic A, Abdoel T H, Smits H L. (2006) Clin Chem Lab Med. 44 180-184.

This invention may be embodied in other forms or carried out in other ways without departing from the spirit or essential characteristics thereof. The present disclosure is therefore to be considered as in all aspects illustrative and not restrictive, the scope of the invention being indicated by the disclosure and description, including any appended Claims, and all changes which come within the meaning and range of equivalency are intended to be embraced therein.

Various references are cited throughout this Specification, each of which is incorporated herein by reference in its entirety.

What is claimed is:

1. A system for the detection and quantitation of cells of interest in a sample, said system comprising:
   (A) a solid support which is a wickable medium suitable for the reception, lateral flow and transport of said sample and any cells therein, wherein the medium supports cells moving over the pre-wetted surface propelled by liquid flow pressure;
   (B) a scaffold or polymer having a repeating unit, which scaffold or polymer is bound covalently or non covalently to the solid support of (A) and applied to the solid support in bands of varying concentrations or dilutions after a first capture area, wherein the scaffold or polymer is a nucleic acid having defined or repeating nucleotide sequence and to which multiple antibodies, peptides or other binding agents are affixed;
   (C) a first capture reagent capable of binding directly or indirectly with the cells of interest in the sample, which first reagent is bound covalently or non covalently to the support of (A) in a capture area, wherein the first capture reagent is one or more antibody, antigen, peptide, protein or ligand configured to bind to an antigen expressed by the cells of interest;
   (D) a surrogate polymer, which is a nucleic acid having defined or repeating complementary nucleotide sequence configured to hybridize with the nucleic acid scaffold or polymer of (B), and which acts as a surrogate marker and is configured for lateral flow in the solid support and for binding directly or indirectly with the cells of interest in the sample; and
   (E) a non-radioactive indicator configured to indicate an amount of scaffold or polymer of (B) which is bound in an assay;
   whereby a presence and the amount of cells of interest in the sample is indicated by the depletion of the surrogate marker such that less surrogate marker is available for binding with the scaffold or polymer of (B) and the intensity of the indicator is reduced.

2. The system of claim 1 wherein
   (A) the solid support is a nitrocellulose membrane.

3. The system of claim 1 wherein the non-radioactive indicator is selected from the group consisting of a label, enzyme, and dye.

4. The system of claim 1 wherein the first capture reagent is one or more antibody.

5. The system of claim 1 wherein the antibody is attached to the scaffold or polymer by noncovalent hybridization via sugar phosphodiester backbone hairpin structures or covalent attachment via chemical bond.

6. The system of claim 1 wherein the scaffold or polymer is streptavidin poly d(T) and the surrogate polymer is poly d(A).

7. The system of claim 1 or claim 6 for detection of CD4+ T cells in an HIV-infected individual wherein the sample is whole blood.

8. The system of claim 7 wherein the first capture reagent is an anti-CD2 antibody.

9. The system of claim 7 which is capable of detecting and quantifying 250 CD4+ T cells/ml or less in a whole blood sample.

10. A test kit for quantitation of one or more cell or cell-type of interest in a sample comprising:
   (A) a solid support which is a wickable medium suitable for the reception, lateral flow and transport of said sample and any cells therein, wherein the medium supports cells moving over the pre-wetted surface propelled by liquid flow pressure;
   (B) a scaffold or polymer having a repeating unit, which scaffold or polymer is bound covalently or non covalently to the solid support of (A) and applied to the solid support in bands of varying concentrations or dilutions after a first capture area, wherein the scaffold or polymer is a nucleic acid having defined or repeating nucleotide sequence and to which multiple antibodies, peptides or other binding agents are affixed;
   (C) a first capture reagent capable of binding directly or indirectly with the cells of interest in the sample, which first reagent is bound covalently or non covalently to the support of (A) in a capture area, wherein the reagent is one or more antibody, antigen, peptide, protein or ligand configured to bind to an antigen expressed by the cells of interest;
   (D) a surrogate polymer which is a nucleic acid having defined or repeating complementary nucleotide sequence configured to hybridize with the nucleic acid scaffold or polymer of (B), and which acts as a surrogate marker and is configured for lateral flow in the solid support and for binding directly or indirectly with the cells of interest in the sample; and
   (E) a non-radioactive indicator configured to indicate an amount of scaffold or polymer of (B) which is bound in an assay;
   whereby a presence and the amount of cells of interest in the sample is indicated by the depletion of the surrogate marker such that less surrogate marker is available for binding with the scaffold or polymer of (B) and the intensity of the indicator is reduced.

11. The test kit of claim 10 wherein the first capture reagent is one or more antibody.

12. The test kit of claim 10 for detection of CD4+ T cells in an HIV-infected individual wherein the sample is whole blood.

13. A method for the manufacture of an detection and quantification strip to be used for detection and quantification of cells of interest in a sample, which strip comprises
- (A) a solid support which is a wickable medium suitable for the reception, lateral flow and transport of said sample and any cells therein, wherein the medium supports cells moving over the pre-wetted surface propelled by liquid flow pressure;
- (B) a scaffold or polymer having a repeating unit, which scaffold or polymer is bound covalently or non covalently to the solid support of (A) and applied to the solid support in bands of varying concentrations or dilutions after a first capture area, wherein the scaffold or polymer is a nucleic acid having defined or repeating nucleotide sequence and to which multiple antibodies, peptides or other binding agents are affixed;
- (C) a first capture reagent capable of binding directly or indirectly with the cells of interest in the sample, which first reagent is bound covalently or non covalently to the support of (A) in a capture area, wherein the reagent is one or more antibody, antigen, peptide, protein or ligand configured to bind to an antigen expressed by the cells of interest;
- (D) a surrogate polymer which is a nucleic acid having defined or repeating complementary nucleotide sequence configured to hybridize with the nucleic acid scaffold or polymer of (B), and which acts as a surrogate marker and is configured for lateral flow in the solid support and for binding directly or indirectly with the cells of interest in the sample; and
- (E) a non-radioactive indicator configured to indicate an amount of scaffold or polymer of (B) which is bound or unbound in the assay;

comprising selecting a liquid deposition device and depositing each or any of the scaffold, first capture reagent, and indicator with said liquid deposition device in a regular and predetermined pattern.

14. The method of claim 13 wherein the liquid deposition device is an inkjet printer.

15. The method of claim 13 wherein
- (A) the solid support is a nitrocellulose membrane.

16. The method of claim 13 wherein the scaffold or polymer is streptavidin poly d(T) and the surrogate polymer is poly d(A).

* * * * *